(12) United States Patent
Morant

(10) Patent No.: US 8,715,994 B2
(45) Date of Patent: May 6, 2014

(54) POLYPEPTIDES HAVING BETA-GLUCOSIDASE AND BETA-XYLOSIDASE ACTIVITY AND POLYNUCLEOTIDES ENCODING SAME

(71) Applicants: Novozymes A/S, Bagsvaerd (DK); Novozymes, Inc., Davis, CA (US)

(72) Inventor: Marc Dominique Morant, Copenhagen (DK)

(73) Assignees: Novozymes A/S, Bagsvaerd (DK); Novozymes Inc., Davis, CA (US)

( * ) Notice: Subject to any disclaimer, the term of this patent is extended or adjusted under 35 U.S.C. 154(b) by 0 days.

(21) Appl. No.: 13/678,638

(22) Filed: Nov. 16, 2012

(65) Prior Publication Data

US 2013/0130325 A1    May 23, 2013

Related U.S. Application Data

(60) Provisional application No. 61/561,446, filed on Nov. 18, 2011.

(51) Int. Cl.
- *C12N 9/24* (2006.01)
- *C12P 19/02* (2006.01)
- *A01N 63/00* (2006.01)
- *A61K 38/54* (2006.01)

(52) U.S. Cl.
USPC ......... 435/200; 424/93.2; 424/94.2; 435/274; 435/68.1

(58) Field of Classification Search
None
See application file for complete search history.

(56) References Cited

U.S. PATENT DOCUMENTS

2008/0201805 A1*  8/2008  Krogh et al. .................. 800/298

OTHER PUBLICATIONS

Guo et al. 2004. Protein tolerance to random amino acid change. PNAS. 101(25):9205-9210.*
Pozzo et al. 2010. Structural and functional analyses of beta-glucosidase 3B from Thermotoga neapolitana: A thermostable three-domain representative of glycoside hydrolase 3. J. Mol. Biol. 397:724-739.*
McClean. 1998. DNA—Basics of structure and analysis: Nucleic acid hybridizations. NDSU. plsc731. p. 1-6.*
Uniprot. 2001. Accession No. Q9KBL8. p. 1-2.*
Uniprot. 1986. Accession No. P04131. p. 1-2.*
Martin et al., UnitProt Accession No. B0D3B6 (2008).
Martin et al., UnitProt Accession No. B0D734 (2008).
Martinet et al., UnitProt Accession No. B8P3Z6 (2009).
Mondego et al., UnitProt Accession No. E2LXM8 (2010).

* cited by examiner

*Primary Examiner* — Anne Kubelik
*Assistant Examiner* — Jeffrey Bolland
(74) *Attorney, Agent, or Firm* — Elias Lambiris

(57) ABSTRACT

The present invention relates to isolated polypeptides having beta-glucosidase activity, beta-xylosidase activity, or beta-glucosidase and beta-xylosidase activity and isolated polynucleotides encoding the polypeptides. The invention also relates to nucleic acid constructs, vectors, and host cells comprising the polynucleotides as well as methods of producing and using the polypeptides.

20 Claims, No Drawings

SEQUENCE LISTING

```
<160> NUMBER OF SEQ ID NOS: 24

<210> SEQ ID NO 1
<211> LENGTH: 2490
<212> TYPE: DNA
<213> ORGANISM: Hohenbuehelia mastrucata

<400> SEQUENCE: 1
atgtctcggt tattcgccag agtcgctctg gcttcgattc tgagtgtcgt ggtcaacgct      60
cagttcaatt tctccttccc cgattgtgcg aatggcccgc tcaagagtaa cgctgtctgc     120
gatacgacgc gttcccctgc tgagcgcgcg aaggcgctca tttcattgtt tactgttccg     180
gagctcatcg cgaacaccgt caatacgagt ccaggtgtac ctcgtttagg gttgcctggt     240
tatcaatggt ggtcagaagc gctggtacgc catccccatt gtggcttcag catggagcta     300
aatatcggcg tgcctagcat ggtattgcag cgtcaaaccc tggcgttaac ttttcggctt     360
ctggggattt cagttccgcc acatcgtttc cacagcctat cattataggc gcggcgtttg     420
acgatgcgct cgtcaagtcc attgccaccg ttatcagcac agaagcccgc gcattcaata     480
attttgggcg agcaggcctt gatttcttca cgccgaacat caacccgttc aaagatcccc     540
gctggggtcg tggccaggaa acacccggag aagatccgtt ccacatctcg caatacgtct     600
tgaacctgat tcaaggttta caaggcggca tcgatccgaa gcctttcctg aaggtcgctg     660
cggactgcaa gcactacgcc gcctacgatc ttgaccactg gaatggtatt gaccgcacag     720
cgttcgatgc catagtgacg acacaggatc tcagcgagtt ttacctcccc ccattccaga     780
```

-continued

```
cttgcgtacg cgacgcgaag gtcgcgtccg tcatgtgcag ttataactcc gtgaacggtg      840
ttccctcgtg cgccaactcg tacctcctcc agacgattct gcgagatcat ggggcttcg       900
gcgaggagcg ctgggtgacg tcggactgtg atgctgtcga caatattttc agcacgcaca      960
atttcacggc aacatatccc caggctgtcg ctgacgcact caaggccggc acggatgttg     1020
actgcggatc cgcgtatgcc ttgcatctgc ccgacgcgtt caatcagtcc ttaatcactc     1080
gtgacgagtt ggagcgtgcc ctagtgcgcc agtatatctc tctcgttcgg tgagaatcgc     1140
gctggttttt tgttagaatt gtcagacatg cttatctcgg cttcctcagc cttggctact     1200
ttgacccacc ttcgactcag ccgttcaggc agctcggctg gtctgatgtt aatgtgccga     1260
gcgcacagac tctcgctcac caagctgctg tcgagggtat cgtcttgctg aagaacgacg     1320
gcacgctgcc tttgaggcgg agcatcaagc gtctggccat cattggtcca tggtccaatg     1380
ccaccacact catgcagggc aattattttg gtaaagcgcc gttcctcatc agtcccatgc     1440
agggtgctgt agatgcgggc ttcaacgtca cgtttgtctt cggcacggct gtcaagggaa     1500
ccacgaccga tggcttcccc gctgcccttg ctgctgctcg gcaagcagat gctgtgatat     1560
cgcgggcgg ccttgacgag accgtcgaga gagaaggaat tgatcgtact gcgataggtt      1620
ggcccgggaa ccagcaggat cttattacac agctggcaag tgtgggcaag ccgttggtcg     1680
tgctgcagtt cggtggtggg cagatcgatg attcggcatt gacatccaat cgtggcgtat     1740
gtcatttatc atatttgttg gactttctct gatcaaacga gacaacaggt caacgccatc     1800
gtatggggag gttaccccggg ccagagtggt ggaactgcga tattcgacat cttaactggg    1860
aaggctgcgc ctgctgggcg gttgcccatc acgcagtacc cggcctcgta tgtcgaccag     1920
gttcctctaa cagatatgac cctgcgtccg agtgccacga atcctggacg cacttacata     1980
tggtactctg caccccagt cttcccgttc ggccatggtt tgcactacac aacattctcg      2040
cttcagtggg cttcgtcgcc gaagtcgcag ttccagattt ctcaacttgt tgccgcagcg     2100
cgcgccgcgt ctaaccctga cttggctaca ctagcgacgt ttaacgtcgc agtcagaaat     2160
accggaagcg taacctcgga ttacgttgcc ctcctcttcg tcaacgggac ggcaggcccc     2220
cagccggcac aaacaaacg cctcgcggcg tatgctcgtc ttcacagcat caaggcgaaa      2280
gcgacctcgc aagcttcctt gaaggtgacg ctcggctcga tagcccgggc ggatgccaat     2340
gggaacttgt ggctacacag cggcgattac gcgatcactg ttgatactcc cggcttgctg     2400
acgcatcgtt ttagcttggt gggacagtct gttcaactca caagcttccc gcaaaatccg     2460
aactcaactt cgaccccatc gccgaaatga                                      2490
```

<210> SEQ ID NO 2
<211> LENGTH: 774
<212> TYPE: PRT
<213> ORGANISM: Hohenbuehelia mastrucata

<400> SEQUENCE: 2

```
Met Ser Arg Leu Phe Ala Arg Val Ala Leu Ala Ser Ile Leu Ser Val
1               5                   10                  15

Val Val Asn Ala Gln Phe Asn Phe Ser Phe Pro Asp Cys Ala Asn Gly
            20                  25                  30

Pro Leu Lys Ser Asn Ala Val Cys Asp Thr Thr Arg Ser Pro Ala Glu
        35                  40                  45

Arg Ala Lys Ala Leu Ile Ser Leu Phe Thr Val Pro Glu Leu Ile Ala
    50                  55                  60
```

```
Asn Thr Val Asn Thr Ser Pro Gly Val Pro Arg Leu Gly Leu Pro Gly
 65                  70                  75                  80

Tyr Gln Trp Trp Ser Glu Ala Leu His Gly Ile Ala Ala Ser Asn Pro
                 85                  90                  95

Gly Val Asn Phe Ser Ala Ser Gly Asp Phe Ser Ser Ala Thr Ser Phe
            100                 105                 110

Pro Gln Pro Ile Ile Ile Gly Ala Ala Phe Asp Asp Ala Leu Val Lys
        115                 120                 125

Ser Ile Ala Thr Val Ile Ser Thr Glu Ala Arg Ala Phe Asn Asn Phe
130                 135                 140

Gly Arg Ala Gly Leu Asp Phe Phe Thr Pro Asn Ile Asn Pro Phe Lys
145                 150                 155                 160

Asp Pro Arg Trp Gly Arg Gly Gln Glu Thr Pro Gly Glu Asp Pro Phe
                165                 170                 175

His Ile Ser Gln Tyr Val Leu Asn Leu Ile Gln Gly Leu Gln Gly Gly
            180                 185                 190

Ile Asp Pro Lys Pro Phe Leu Lys Val Ala Ala Asp Cys Lys His Tyr
        195                 200                 205

Ala Ala Tyr Asp Leu Asp His Trp Asn Gly Ile Asp Arg Thr Ala Phe
210                 215                 220

Asp Ala Ile Val Thr Thr Gln Asp Leu Ser Glu Phe Tyr Leu Pro Pro
225                 230                 235                 240

Phe Gln Thr Cys Val Arg Asp Ala Lys Val Ala Ser Val Met Cys Ser
                245                 250                 255

Tyr Asn Ser Val Asn Gly Val Pro Ser Cys Ala Asn Ser Tyr Leu Leu
            260                 265                 270

Gln Thr Ile Leu Arg Asp His Trp Gly Phe Gly Glu Glu Arg Trp Val
        275                 280                 285

Thr Ser Asp Cys Asp Ala Val Asp Asn Ile Phe Ser Thr His Asn Phe
290                 295                 300

Thr Ala Thr Tyr Pro Gln Ala Val Ala Asp Ala Leu Lys Ala Gly Thr
305                 310                 315                 320

Asp Val Asp Cys Gly Ser Ala Tyr Ala Leu His Leu Pro Asp Ala Phe
                325                 330                 335

Asn Gln Ser Leu Ile Thr Arg Asp Glu Leu Glu Arg Ala Leu Val Arg
            340                 345                 350

Gln Tyr Ile Ser Leu Val Arg Leu Gly Tyr Phe Asp Pro Pro Ser Thr
        355                 360                 365

Gln Pro Phe Arg Gln Leu Gly Trp Ser Asp Val Asn Val Pro Ser Ala
370                 375                 380

Gln Thr Leu Ala His Gln Ala Val Glu Gly Ile Val Leu Leu Lys
385                 390                 395                 400

Asn Asp Gly Thr Leu Pro Leu Arg Arg Ser Ile Lys Arg Leu Ala Ile
                405                 410                 415

Ile Gly Pro Trp Ser Asn Ala Thr Thr Leu Met Gln Gly Asn Tyr Phe
            420                 425                 430

Gly Lys Ala Pro Phe Leu Ile Ser Pro Met Gln Gly Ala Val Asp Ala
        435                 440                 445

Gly Phe Asn Val Thr Phe Val Phe Gly Thr Ala Val Lys Gly Thr Thr
450                 455                 460

Thr Asp Gly Phe Pro Ala Ala Leu Ala Ala Arg Gln Ala Asp Ala
465                 470                 475                 480

Val Ile Phe Ala Gly Gly Leu Asp Glu Thr Val Glu Arg Glu Gly Ile
                485                 490                 495
```

```
Asp Arg Thr Ala Ile Gly Trp Pro Gly Asn Gln Gln Asp Leu Ile Thr
            500                 505                 510

Gln Leu Ala Ser Val Gly Lys Pro Leu Val Val Leu Gln Phe Gly Gly
            515                 520                 525

Gly Gln Ile Asp Asp Ser Ala Leu Thr Ser Asn Arg Gly Val Asn Ala
        530                 535                 540

Ile Val Trp Gly Gly Tyr Pro Gly Gln Ser Gly Gly Thr Ala Ile Phe
545                 550                 555                 560

Asp Ile Leu Thr Gly Lys Ala Ala Pro Ala Gly Arg Leu Pro Ile Thr
                565                 570                 575

Gln Tyr Pro Ala Ser Tyr Val Asp Gln Val Pro Leu Thr Asp Met Thr
            580                 585                 590

Leu Arg Pro Ser Ala Thr Asn Pro Gly Arg Thr Tyr Ile Trp Tyr Ser
        595                 600                 605

Gly Thr Pro Val Phe Pro Phe Gly His Gly Leu His Tyr Thr Thr Phe
    610                 615                 620

Ser Leu Gln Trp Ala Ser Ser Pro Lys Ser Gln Phe Gln Ile Ser Gln
625                 630                 635                 640

Leu Val Ala Ala Ala Arg Ala Ala Ser Asn Pro Asp Leu Ala Thr Leu
                645                 650                 655

Ala Thr Phe Asn Val Ala Val Arg Asn Thr Gly Ser Val Thr Ser Asp
            660                 665                 670

Tyr Val Ala Leu Leu Phe Val Asn Gly Thr Ala Gly Pro Gln Pro Ala
        675                 680                 685

Pro Asn Lys Arg Leu Ala Ala Tyr Ala Arg Leu His Ser Ile Lys Ala
    690                 695                 700

Lys Ala Thr Ser Gln Ala Ser Leu Lys Val Thr Leu Gly Ser Ile Ala
705                 710                 715                 720

Arg Ala Asp Ala Asn Gly Asn Leu Trp Leu His Ser Gly Asp Tyr Ala
                725                 730                 735

Ile Thr Val Asp Thr Pro Gly Leu Leu Thr His Arg Phe Ser Leu Val
            740                 745                 750

Gly Gln Ser Val Gln Leu Thr Ser Phe Pro Gln Asn Pro Asn Ser Thr
        755                 760                 765

Ser Thr Pro Ser Pro Lys
    770

<210> SEQ ID NO 3
<211> LENGTH: 3247
<212> TYPE: DNA
<213> ORGANISM: Hohenbuehelia mastrucata

<400> SEQUENCE: 3
atgagagggc tactgtcttt tacgctcctt tcaatctatt gtcttccgat tttcgctgtc      60
gagaacctct tgggcgtccg cgatgacttg cacttcagtt tagaagcacg cgcagccaac     120
aaggatggct ccatcccaat ttacaagaac cccaaagcct cgattgaggc tcgcgtcaat     180
gatttactcc cacgtatgac ggtggaagaa aaaatggccc aactgtgagt cttcatttgc     240
ttgattgctc cattgctaag gtacgcccga tagaatccaa ggagacatga acgggtggat     300
gaatctgaac gatccgttgg ataacacgaa ggttttcaat caaacaggcc tggtaatatc     360
ttcacaatgc gcggtcattt gggtgcttgc tcatctgtcc ttaggaagag atgatgagat     420
tgaaaggtgg ctcgatctgg cgggggtatc tgatgccttg gacaaatttt gtcttcggcg     480
tcaacgttgg gcaacggtat ctgatggaga acactactct gggaatccca gcactcattc     540
```

```
aatccgaggg taagactttt cgtttggcaa tgtgtcgatt tttcatatgg gactaaggag    600
aaatgcttac aggacttcac ggcttcacca ataatggcac aatattccct tcgcctattg    660
gcttggccgc gtcatttgat gtcgacctcg tctcgaaagt ggcggcttcc atttccactg    720
aggctgaggg ccttggaatc aaccacatct tcgcgccagt tctggattta tcccgtgagc    780
ttcgatgggg ccgcgttgaa gagaactacg gtgaagaccc attcctcact ggcgaaatcg    840
gacacgcgta cgtctcgggc ctccagtccg gtaaacgtcg gaatgtcagc tctacagcta    900
tcgcgcgcat ggcagcgact tgcaaacact tcgcagcatt tggcagtcca cagggtggcc    960
tgtaggtttt tatatcctgt gaaagcgttg gatactctct aatgaggatg ccagtaacct   1020
tgctcaggtt tcgggtggcg agcgggagct ccgtacaaca ttcctcaagc ccttcgaccg   1080
cgcttgtttg caaagcatga ccataatgac agcctactcc agctacgacg gcattcctgc   1140
tattgccaac gatcgtaggt tttcacattg cttgttgtag gctgtgcatt cttgtgttga   1200
tgctgctatc gtttatagat atgctcatcg atattgtaag taccatatac cgctcgctat   1260
atctactgag tgaagctcac atatactcca tgacacagct tcgcaaagag tggggataca   1320
aatattgggt cgtctccgat gcaggctctg tcgacttgct tatcactctt cacggcacct   1380
gtgcgactag ggagtgtgcg gcgaagacag ccttagaaaa ggggctttcg ggcgagatgg   1440
gcggcggcac ctacacatac ttgaccctac ctggtacgag tctccttttt cgcgaagaat   1500
accagcctca ttatgtctcc agaccagatc aaggctggca ccgtgagcat gcaagcactt   1560
gacactaccg tcagttacat gctccgcacc aaatttccca tgggcctgtt cgagagtaag   1620
gtgctcctaa cgttcatcgc catttactga cgagcatcag acccatacccc gtacgacgat   1680
tggaattcca cattacgcac ggctgcaact caacaaatcc tacgtactgc tgaccgcgag   1740
agcattgtcc ttctcgagaa tcaccagaac acgctcccct taaagaagag catcggatct   1800
atcgccgtca tagggccgca cgctgatcgt gtctctgtat gtatcccttg gctcgccaat   1860
agcttgatca ctaaattcac cttttgcgatc cgtagttcgg agattacgtg ttcttcaacg   1920
ctactctaaa cggcgttact cctttggctg gcttcaaaca ggttctcgcg gatacgtccg   1980
tcaaaatcaa ctacgcggag ggctccaaac tgtggtcaaa cgatcagagc ggatttttcgg  2040
ccgcagtttc tgctgcgcag tcatctgatg ttgctgtcgt tttagttggg acttggtctt   2100
tagaccagac tctattgtgg acgcccggaa caaacgcgac gactggcgag cacgttgacg   2160
ttgctgatct cggtcttgtc ggagcgcaac tcgaccttgt aaaggcagtc aaggccgcag   2220
gaaagcctac ggtcgttgtc ttcgtcagcg gcaaaccggt ggcagagcct tggattcaag   2280
ctagtagggc gcatcttgcc atgtgctgcg gctgttttc tgatttgatt tgcttttta    2340
agatgctgat gcagtgatcc agcagtttta ccctggtgaa ttaggtggtt tggcgcttgc   2400
tgaggttatt tttggtgatg tgaatccttc tggtaatctt tgccgttctt gtcatttac   2460
tatctgcagc acttatcagt ccaacaggga agttgccggt atctttccct cacgacgtcg   2520
gaaccactcc agttttctac aactacctca aaggcagccg tccctagac cctggtgccg    2580
tcctggataa cggaaatctt cagtttggcc atcaggttcg ttcctcagct gatcctaact   2640
acatattttg attctcaatc aatgaatgtt ccattcagta cgtattaaac accccagtgc   2700
ccctatggag cttcggccat ggcctcagtt acacaacatt ccaatagtat gtctctcgga   2760
gcatcattcg gagctgttca ctcaatcaaa cttcatagct ccggtcttac tttgtcccct   2820
tctaagatag gacgtaacag cgatttcacc gtcaccgtca ctgtccggaa tacgggttcc   2880
atgacaggca aagaagtcgt ccaggtatgt aaattatgta atccaaattc gaggagttaa   2940
```

```
ataacatcat gatcgtgtgt aggtttacct gaccgacgtg cttgcttcag tcgtcacgcc   3000
aaatcaggaa ttggtcggat tccagaaagt cgaaattccg tacgtgtgac ttgtcggttt   3060
ctgtcgattt ctcattgact ttcattttag tgccggaggt tcaaaaacag tatctatcaa   3120
ggtcaactcg gagcagctgg cagtgtggtc acccagcaat gcgtgggtgg ttgagcctgg   3180
ccagtttgcg atcaaagttg ggacgagcga ccagacattt gcgaatgcga cgctgacggt   3240
tacatga                                                              3247
```

<210> SEQ ID NO 4
<211> LENGTH: 799
<212> TYPE: PRT
<213> ORGANISM: Hohenbuehelia mastrucata

<400> SEQUENCE: 4

```
Met Arg Gly Leu Leu Ser Phe Thr Leu Leu Ser Ile Tyr Cys Leu Pro
1               5                   10                  15

Ile Phe Ala Val Glu Asn Leu Leu Gly Val Arg Asp Asp Leu His Phe
            20                  25                  30

Ser Leu Glu Ala Arg Ala Ala Asn Lys Asp Gly Ser Ile Pro Ile Tyr
        35                  40                  45

Lys Asn Pro Lys Ala Ser Ile Glu Ala Arg Val Asn Asp Leu Leu Pro
    50                  55                  60

Arg Met Thr Val Glu Glu Lys Met Ala Gln Leu Ile Gln Gly Asp Met
65                  70                  75                  80

Asn Gly Trp Met Asn Leu Asn Asp Pro Leu Asp Asn Thr Lys Val Phe
                85                  90                  95

Asn Gln Thr Gly Leu Glu Glu Met Met Arg Leu Lys Gly Gly Ser Ile
            100                 105                 110

Trp Ala Gly Tyr Leu Met Pro Trp Asp Lys Phe Val Phe Gly Val Asn
        115                 120                 125

Val Gly Gln Arg Tyr Leu Met Glu Asn Thr Thr Leu Gly Ile Pro Ala
    130                 135                 140

Leu Ile Gln Ser Glu Gly Leu His Gly Phe Thr Asn Asn Gly Thr Ile
145                 150                 155                 160

Phe Pro Ser Pro Ile Gly Leu Ala Ala Ser Phe Asp Val Asp Leu Val
                165                 170                 175

Ser Lys Val Ala Ala Ser Ile Ser Thr Glu Ala Glu Gly Leu Gly Ile
            180                 185                 190

Asn His Ile Phe Ala Pro Val Leu Asp Leu Ser Arg Glu Leu Arg Trp
        195                 200                 205

Gly Arg Val Glu Glu Asn Tyr Gly Glu Asp Pro Phe Leu Thr Gly Glu
    210                 215                 220

Ile Gly His Ala Tyr Val Ser Gly Leu Gln Ser Gly Lys Arg Arg Asn
225                 230                 235                 240

Val Ser Ser Thr Ala Ile Ala Arg Met Ala Ala Thr Cys Lys His Phe
                245                 250                 255

Ala Ala Phe Gly Ser Pro Gln Gly Gly Leu Asn Leu Ala Gln Val Ser
            260                 265                 270

Gly Gly Glu Arg Glu Leu Arg Thr Thr Phe Leu Lys Pro Phe Asp Arg
        275                 280                 285

Ala Cys Leu Gln Ser Met Thr Ile Met Thr Ala Tyr Ser Ser Tyr Asp
    290                 295                 300

Gly Ile Pro Ala Ile Ala Asn Asp His Met Leu Ile Asp Ile Leu Arg
305                 310                 315                 320
```

-continued

Lys Glu Trp Gly Tyr Lys Tyr Trp Val Val Ser Asp Ala Gly Ser Val
                325                 330                 335

Asp Leu Leu Ile Thr Leu His Gly Thr Cys Ala Thr Arg Glu Cys Ala
                340                 345                 350

Ala Lys Thr Ala Leu Glu Lys Gly Leu Ser Gly Glu Met Gly Gly Gly
                355                 360                 365

Thr Tyr Thr Tyr Leu Thr Leu Pro Asp Gln Ile Lys Ala Gly Thr Val
370                 375                 380

Ser Met Gln Ala Leu Asp Thr Thr Val Ser Tyr Met Leu Arg Thr Lys
385                 390                 395                 400

Phe Ser Met Gly Leu Phe Glu Asn Pro Tyr Pro Tyr Asp Asp Trp Asn
                405                 410                 415

Ser Thr Leu Arg Thr Ala Ala Thr Gln Gln Ile Leu Arg Thr Ala Asp
                420                 425                 430

Arg Glu Ser Ile Val Leu Leu Glu Asn His Gln Asn Thr Leu Pro Leu
                435                 440                 445

Lys Lys Ser Ile Gly Ser Ile Ala Val Ile Gly Pro His Ala Asp Arg
                450                 455                 460

Val Ser Phe Gly Asp Tyr Val Phe Phe Asn Ala Thr Leu Asn Gly Val
465                 470                 475                 480

Thr Pro Leu Ala Gly Phe Lys Gln Val Leu Ala Asp Thr Ser Val Lys
                485                 490                 495

Ile Asn Tyr Ala Glu Gly Ser Lys Leu Trp Ser Asn Asp Gln Ser Gly
                500                 505                 510

Phe Ser Ala Ala Val Ser Ala Ala Gln Ser Ser Asp Val Ala Val Val
                515                 520                 525

Leu Val Gly Thr Trp Ser Leu Asp Gln Thr Leu Leu Trp Thr Pro Gly
                530                 535                 540

Thr Asn Ala Thr Thr Gly Glu His Val Asp Val Ala Asp Leu Gly Leu
545                 550                 555                 560

Val Gly Ala Gln Leu Asp Leu Val Lys Ala Val Lys Ala Ala Gly Lys
                565                 570                 575

Pro Thr Val Val Phe Val Ser Gly Lys Pro Val Ala Glu Pro Trp
                580                 585                 590

Ile Gln Ala Met Ile Gln Gln Phe Tyr Pro Gly Glu Leu Gly Gly Leu
                595                 600                 605

Ala Leu Ala Glu Val Ile Phe Gly Asp Val Asn Pro Ser Gly Lys Leu
                610                 615                 620

Pro Val Ser Phe Pro His Asp Val Gly Thr Thr Pro Val Phe Tyr Asn
625                 630                 635                 640

Tyr Leu Lys Gly Ser Arg Pro Leu Asp Pro Gly Ala Val Leu Asp Asn
                645                 650                 655

Gly Asn Leu Gln Phe Gly His Gln Tyr Val Leu Asn Thr Pro Val Pro
                660                 665                 670

Leu Trp Ser Phe Gly His Gly Leu Ser Tyr Thr Thr Phe Gln Tyr Ser
                675                 680                 685

Gly Leu Thr Leu Ser Pro Ser Lys Ile Gly Arg Asn Ser Asp Phe Thr
                690                 695                 700

Val Thr Val Thr Val Arg Asn Thr Gly Ser Met Thr Gly Lys Glu Val
705                 710                 715                 720

Val Gln Val Tyr Leu Thr Asp Val Leu Ala Ser Val Val Thr Pro Asn
                725                 730                 735

```
Gln Glu Leu Val Gly Phe Gln Lys Val Glu Ile Pro Ala Gly Ser
            740                 745                 750
Lys Thr Val Ser Ile Lys Val Asn Ser Glu Gln Leu Ala Val Trp Ser
        755                 760                 765
Pro Ser Asn Ala Trp Val Val Glu Pro Gly Gln Phe Ala Ile Lys Val
    770                 775                 780
Gly Thr Ser Asp Gln Thr Phe Ala Asn Ala Thr Leu Thr Val Thr
785                 790                 795

<210> SEQ ID NO 5
<211> LENGTH: 3290
<212> TYPE: DNA
<213> ORGANISM: Hohenbuehelia mastrucata

<400> SEQUENCE: 5
```

| | | | | | |
|---|---|---|---|---|---|
| atggccaccc | tcaccctgct | catcgcagca | gcggccgttg | ctgcacaaca | gtcttcgctg | 60 |
| gcactttcgg | tgacaacgac | gctcgtctcg | tcatcgttcg | cagcgtcttc | catcgagact | 120 |
| tccattcaac | cttctagcgt | gttttccagc | atcacagtct | cggtttctgg | cgaacccact | 180 |
| agcacgtcgc | tgtcggcttc | gtcatccgcc | gaaccggttc | tgcaatcggt | agccccgtcg | 240 |
| ataccaatca | ctcagtacac | cttttcgcca | tttccaactc | catctcgctc | tccagtaccg | 300 |
| ggagtatttg | tcgagacaga | tccgtcggat | cctcctccag | tcaatgcccc | agttattcca | 360 |
| gactttgcac | cagcttgggc | gaaagcttac | gccaaggcaa | aggagctggt | cagcaaaaat | 420 |
| attcaattgc | tattaccaca | cattaatcct | ccttaggtct | cgacattcac | actcgaggaa | 480 |
| aaggtcaatg | tcaccactgg | tgtcggctgg | atgaacgggc | tgtgtgttgg | aaatattcct | 540 |
| gctgtaaaag | actggccggg | tctctgttta | gaggactctc | ctctaggcat | acgtttcgcc | 600 |
| gactttgtca | ctgcgtttcc | aactggcgtc | aataccgcgt | ctacgtgagt | ccttcgaacc | 660 |
| ttttccgtct | ttcattaata | ttcaagcgtc | attctcaggt | tcaaccgccg | tctcatgcgc | 720 |
| cttcgtggtc | tcttcatggg | ccgtgaacac | gttggaaagg | gtgtcaatgt | tgctcttggg | 780 |
| cccatgatga | acctcggcag | gattgctcaa | ggcggtcgga | attgggaagg | tttcggttcg | 840 |
| taacctttac | gatgctcgcc | ttcgaccacc | ctaatttatg | acgatcactc | aggcgcggat | 900 |
| ccctacctag | ctggtgaagg | taagcgagcg | attgtctctt | tgcgatagca | tgctccaact | 960 |
| tccgcgcagc | ttcgtacgag | actatcctcg | gtatgcaaga | aggaggtgtg | caggcatgtg | 1020 |
| cgaagcattt | catcgacaag | tacgtataca | ctaccctctc | gtccgtgctc | tctcaaactt | 1080 |
| atattattcc | agcgagcaag | aacacaagcg | caccacatca | tcctccgatg | tcgacgaccg | 1140 |
| gacgcaacac | gagatttacg | cacacccgtt | cctgcgcagt | gtcatggctg | gcgtgacgag | 1200 |
| cgtcatgtgc | agttacagta | agtgtatcat | cccttcattg | gcatcaggaa | ttgaaattaa | 1260 |
| ttgtgtttca | gaccaagtca | acggtaccta | cgcttgcgag | aacgacaaaa | tgctcaacga | 1320 |
| tgtgcttaag | cgcgagtttg | ggttccaagg | ctgtaagtag | tcattcactc | tgtgttacgc | 1380 |
| aatgtacggt | atctgactct | tcgcgcagtt | gtcatgtccg | actggcaggc | tacgcactca | 1440 |
| accatctcgg | ccattacggg | tctcgatgtg | agaccgcagc | tctctgaatt | cctcacacaa | 1500 |
| atctgatctc | cgtgtagatg | accatgcctg | gcgacgtgac | gttcagctca | ggcgattcct | 1560 |
| acttcggcgg | caatctgacc | gcctacgtcc | agaacggcac | aatccccgag | tcgcgcgttg | 1620 |
| acgacatggt | atacttcatc | ccacctcttc | cttttcttcc | gctgaccggt | tcgaccaggc | 1680 |
| tacgcgcatc | ctcgctggct | ggtacccttct | caagcaagac | gcggaagact | tccccgccac | 1740 |
| caacttcaac | gccttcaagc | cagatgacga | ggcgacaaac | aagcacgtcg | atgtccaggc | 1800 |

-continued

```
cgagggtgtc gataagctcg tgcgcgacat cggtgccgcg agcactgtcc tgctgaagaa    1860
caagggcaac gtgttgccac tacgcaagcc gcggagcctt gtccttgtag gcagcgacgc    1920
gggtccggcg cgcattggtc cgaacggggtt cgctgatcaa ggcggcgttg atggtgtctt    1980
```

```
cgagggtgtc gataagctcg tgcgcgacat cggtgccgcg agcactgtcc tgctgaagaa    1860
caagggcaac gtgttgccac tacgcaagcc gcggagcctt gtccttgtag gcagcgacgc    1920
gggtccggcg cgcattggtc cgaacgggtt cgctgatcaa ggcggcgttg atggtgtctt    1980
ggctatgggt tggggtagtg ggacagcgaa cttcacttat ctcgtttcgg ttcgtcgaat    2040
tcttccttgt ggaagcaaga gcgtgcgctt acctgagtgt agccgttgga agcgattcag    2100
cgtcgcgctc gcaaggatca cacgtccatg tcgtggttcc tcgacgactt tgaccttgcg    2160
agagccggca acgtcgtgat cggcaagacg gcggcgcttg tcttcgtgaa ctcggattct    2220
ggcgaacagt acattaccgt cgatggtaac gagggcgatc ggtatgcagg cctttctaac    2280
tcgccacaac cgcaatacta acttgtaata tttcatttta gcaagaatct gacggcgtgg    2340
cacagcggcg acgatctcat tctcgctgtt gcggcacaga acaacaatac cattgtcatt    2400
acgcacagcg tcggcccgct tattgtcgag ccttggattg accacccgaa tgtcactgct    2460
gtcctctggg caggtgtgtc ggggacagag acgggtaacg ctataaagga cgtgctgtat    2520
ggcgactgga acccttctgg gcgcctccca tacacgatcg cgaagaaggt ggaggactac    2580
tccgcacagc tcgtccttgg aggtggcggc gatgagaaca ttctggcact gccgtatacg    2640
gagggcttgg agattgatta tcgtcatttt gacgcggtga gcattcatct tgtttatgtt    2700
tcgtttttgta gacttacgca atgtgattgc tttaaagaaa aacatcacac cgcgcttcga    2760
gtttggcttt gggttgagct ataccaagtt ctcgtacggc aacctggaga tcgaacgcgt    2820
accgagcaac gacggcgtcc aggccgacct tgaggaagct tgggagcaag gaaaggctag    2880
tccgcatggt caaggctcga cgtcgagct atggcttcac cgacctgcgt tccgcgtctc    2940
gttccatgtc aagaacatcg gtaagctgtt tggtggcgac gtacgtgttt atttcttcct    3000
tccttccctg cgaagaccag gatctgacct tatttcgcaa tacccagatt ccgcagctgt    3060
acgtgaactt cccagcgtca tccggcgaac cgccatcggt gctcaggggc ttcacgaacg    3120
tcgagctgct gcccgggcag acgaagcgcc tcgagttgct gctctcgcga tatgacttga    3180
gcgtgtggga cacagtcgca cagggttggc gcaagccgaa aggcaccatc cgcgtcagtg    3240
tcggcgcgag cagcagggat ttcaggctga agggcagcat tcctgtttaa                3290
```

<210> SEQ ID NO 6
<211> LENGTH: 858
<212> TYPE: PRT
<213> ORGANISM: Hohenbuehelia mastrucata

<400> SEQUENCE: 6

```
Met Ala Thr Leu Thr Leu Leu Ile Ala Ala Ala Val Ala Ala Gln
1               5                  10                  15

Gln Ser Ser Leu Ala Leu Ser Val Thr Thr Thr Leu Val Ser Ser
                20                  25                  30

Phe Ala Ala Ser Ser Ile Glu Thr Ser Ile Gln Pro Ser Ser Val Phe
            35                  40                  45

Ser Ser Ile Thr Val Ser Val Ser Gly Glu Pro Thr Ser Thr Ser Leu
        50                  55                  60

Ser Ala Ser Ser Ser Ala Glu Pro Val Leu Gln Ser Val Ala Pro Ser
65                  70                  75                  80

Ile Pro Ile Thr Gln Tyr Thr Phe Ser Pro Phe Pro Thr Pro Ser Arg
                85                  90                  95

Ser Pro Val Pro Gly Val Phe Val Glu Thr Asp Pro Ser Asp Pro Pro
            100                 105                 110
```

-continued

Pro Val Asn Ala Pro Val Ile Pro Asp Phe Ala Pro Ala Trp Ala Lys
            115                 120                 125

Ala Tyr Ala Lys Ala Lys Glu Leu Val Ser Thr Phe Thr Leu Glu Glu
    130                 135                 140

Lys Val Asn Val Thr Thr Gly Val Gly Trp Met Asn Gly Leu Cys Val
145                 150                 155                 160

Gly Asn Ile Pro Ala Val Lys Asp Trp Pro Gly Leu Cys Leu Glu Asp
                165                 170                 175

Ser Pro Leu Gly Ile Arg Phe Ala Asp Phe Val Thr Ala Phe Pro Thr
            180                 185                 190

Gly Val Asn Thr Ala Ser Thr Phe Asn Arg Arg Leu Met Arg Leu Arg
        195                 200                 205

Gly Leu Phe Met Gly Arg Glu His Val Gly Lys Gly Val Asn Val Ala
    210                 215                 220

Leu Gly Pro Met Met Asn Leu Gly Arg Ile Ala Gln Gly Gly Arg Asn
225                 230                 235                 240

Trp Glu Gly Phe Gly Ala Asp Pro Tyr Leu Ala Gly Glu Ala Ser Tyr
                245                 250                 255

Glu Thr Ile Leu Gly Met Gln Glu Gly Gly Val Gln Ala Cys Ala Lys
            260                 265                 270

His Phe Ile Asp Asn Glu Gln Glu His Lys Arg Thr Thr Ser Ser Ser
        275                 280                 285

Asp Val Asp Asp Arg Thr Gln His Glu Ile Tyr Ala His Pro Phe Leu
    290                 295                 300

Arg Ser Val Met Ala Gly Val Thr Ser Val Met Cys Ser Tyr Asn Gln
305                 310                 315                 320

Val Asn Gly Thr Tyr Ala Cys Glu Asn Asp Lys Met Leu Asn Asp Val
                325                 330                 335

Leu Lys Arg Glu Phe Gly Phe Gln Gly Phe Val Met Ser Asp Trp Gln
            340                 345                 350

Ala Thr His Ser Thr Ile Ser Ala Ile Thr Gly Leu Asp Met Thr Met
        355                 360                 365

Pro Gly Asp Val Thr Phe Ser Ser Gly Asp Ser Tyr Phe Gly Gly Asn
    370                 375                 380

Leu Thr Ala Tyr Val Gln Asn Gly Thr Ile Pro Glu Ser Arg Val Asp
385                 390                 395                 400

Asp Met Ala Thr Arg Ile Leu Ala Gly Trp Tyr Leu Leu Lys Gln Asp
                405                 410                 415

Ala Glu Asp Phe Pro Ala Thr Asn Phe Asn Ala Phe Lys Pro Asp Asp
            420                 425                 430

Glu Ala Thr Asn Lys His Val Asp Val Gln Ala Glu Gly Val Asp Lys
        435                 440                 445

Leu Val Arg Asp Ile Gly Ala Ala Ser Thr Val Leu Leu Lys Asn Lys
    450                 455                 460

Gly Asn Val Leu Pro Leu Arg Lys Pro Arg Ser Leu Val Leu Val Gly
465                 470                 475                 480

Ser Asp Ala Gly Pro Ala Arg Ile Gly Pro Asn Gly Phe Ala Asp Gln
                485                 490                 495

Gly Gly Val Asp Gly Val Leu Ala Met Gly Trp Gly Ser Gly Thr Ala
            500                 505                 510

Asn Phe Thr Tyr Leu Val Ser Pro Leu Glu Ala Ile Gln Arg Arg Ala
        515                 520                 525

Arg Lys Asp His Thr Ser Met Ser Trp Phe Leu Asp Asp Phe Asp Leu
    530                 535                 540

```
Ala Arg Ala Gly Asn Val Val Ile Gly Lys Thr Ala Ala Leu Val Phe
545                 550                 555                 560

Val Asn Ser Asp Ser Gly Glu Gln Tyr Ile Thr Val Asp Gly Asn Glu
            565                 570                 575

Gly Asp Arg Lys Asn Leu Thr Ala Trp His Ser Gly Asp Leu Ile
        580                 585                 590

Leu Ala Val Ala Ala Gln Asn Asn Asn Thr Ile Val Ile Thr His Ser
        595                 600                 605

Val Gly Pro Leu Ile Val Glu Pro Trp Ile Asp His Pro Asn Val Thr
610                 615                 620

Ala Val Leu Trp Ala Gly Val Ser Gly Thr Glu Thr Gly Asn Ala Ile
625                 630                 635                 640

Lys Asp Val Leu Tyr Gly Asp Trp Asn Pro Ser Gly Arg Leu Pro Tyr
                645                 650                 655

Thr Ile Ala Lys Lys Val Glu Asp Tyr Ser Ala Gln Leu Val Leu Gly
                660                 665                 670

Gly Gly Gly Asp Glu Asn Ile Leu Ala Leu Pro Tyr Thr Glu Gly Leu
        675                 680                 685

Glu Ile Asp Tyr Arg His Phe Asp Ala Lys Asn Ile Thr Pro Arg Phe
690                 695                 700

Glu Phe Gly Phe Gly Leu Ser Tyr Thr Lys Phe Ser Tyr Gly Asn Leu
705                 710                 715                 720

Glu Ile Glu Arg Val Pro Ser Asn Asp Gly Val Gln Ala Asp Leu Glu
                725                 730                 735

Glu Ala Trp Glu Gln Gly Lys Ala Ser Pro His Gly Gln Gly Ser Ser
                740                 745                 750

Val Glu Leu Trp Leu His Arg Pro Ala Phe Arg Val Ser Phe His Val
            755                 760                 765

Lys Asn Ile Gly Lys Leu Phe Gly Gly Asp Ile Pro Gln Leu Tyr Val
770                 775                 780

Asn Phe Pro Ala Ser Ser Gly Glu Pro Ser Val Leu Arg Gly Phe
785                 790                 795                 800

Thr Asn Val Glu Leu Leu Pro Gly Gln Thr Lys Arg Leu Glu Leu Leu
                805                 810                 815

Leu Ser Arg Tyr Asp Leu Ser Val Trp Asp Thr Val Ala Gln Gly Trp
        820                 825                 830

Arg Lys Pro Lys Gly Thr Ile Arg Val Ser Val Gly Ala Ser Ser Arg
        835                 840                 845

Asp Phe Arg Leu Lys Gly Ser Ile Pro Val
        850                 855
```

<210> SEQ ID NO 7
<211> LENGTH: 3221
<212> TYPE: DNA
<213> ORGANISM: Hohenbuehelia mastrucata

<400> SEQUENCE: 7

| | | |
|---|---|---|
| atggctcgct tgatctgctt cctctctttg ctctcatccg ccagcgcgtt cactcttcgt | 60 |
| cagttgcatc gaaatcgcc tctaggcatt cactaacgca tctctaggat catggacgga | 120 |
| tgcctacaat ctcgccaaca atgctgtcac acaaatgact ctcgatgaaa aggtcggaat | 180 |
| cttaaccggc gttggccagt ctccagtgc gtcatcacgc gagccctact cgcgaaatcc | 240 |
| cgtacagctg attcattgca tcaggccgct gcgttggtga tacacacccc gtctcgcgac | 300 |
| tcggcatccc ctccatctgc ttccaggacg gcccagccgg cgtgcgcgcc accaaagggg | 360 |

-continued

```
tgactggttt ccctacaggc atcaacaccg catcgacctt cagtagaagg ctcatgcgcg      420
cacgcggtgt cgcgctcggc gaggaatttc gcgggaaggg tataaagtga gtccgcatgc      480
tacgcccgct cgccgtgatt ctcaccgctt ccatccatac agcgtcttcc tgggcccagc      540
gatggacatt gtgagcgctg cttcgcgatg caatatcgtc cacactcgtc tgatcacgct      600
cacagatgcg aaatcccaag gctggacgcg cttgggaaag gtgtgtgaaa ttttgtcata      660
tcaatcatcc atacggcccg tcggaatgcc catgcctgtt actcttccgc gctatctttt      720
tgattgtgcc gcagggtcgg aacagcgcag tagcattgag cgatagattc tgaggcccga      780
cattacgtct ttgcacgacg catcatcact tgccatatca caatcatttc tcgcctgcaa      840 cttactttt atctagtttt ggccccgatc cgtacctcaa cggcgaaggc gcgttcgaaa      900
ccatcacagg cgtccagagc gtcggcgtcc aagcatgcgc aaaacatttc gtcggaaaca      960
accaagaaca ctggcgctac ggcgcttcgt cgaacatcga cgaccgaacc atgaacgaaa     1020
tctacgcgta tccgttttat cggagtatag atgtatgtga gatattcttc agacggccaa     1080
agggactaaa cttacgcgtt ctgaataggc cggcgtgacg tccataatgt gtgcgtacaa     1140
tcgtgttaac gggacatcgt cgtgccataa cgcgaacatg ctcggaaata acggccttct     1200
acgcaagaat ggctttatgg gtgcgtttta ttcagcattt ttggcacgtc attgatcgac     1260
ctctattcat ctaggctacg tcgtcagcga ttggggcgct acgcatgaca cagccgccga     1320
taatgctaac gctggtctcg agatggagca acccggcgat ttcatcgtga ttggcggagg     1380
tgtctacaac aatctgctca gcggtctcaa gcccgccgtg aacagcggga aagtatctac     1440
cgcggtgagc tcaatgacat tttctgccca acgtcaagcg ctgagcatca tccatttccg     1500
ctcttagcgc ctaaatgaaa tggtagcgcg agtccttgcc ggatggtacc gcctcggcca     1560
ggactcggtg tgtccattca tcgactcaaa ttcttcgatt acgcgtgctc attaagactt     1620
cgattgacag ggatacgcgg cacccaactt cgacacgcag cactccgacg gctcggggtc     1680
cctcaacgag aacatttccg tccgctccga cgcacacacc gccctcgtgc gcgaaatcgc     1740
ctcagcatcg gcagtactgc tcaagaacaa tcgcaccacc ctcggcgcgg gcggccctac     1800
tgtccgtggt ctgcctgttg cgcaggcgca agtacacagc atggcggtag ttggactcga     1860
tgcgatgatg cccgggaagg actgtgggga cctgaataca tgcaataagg gtaccattac     1920
gacggggtat gctttttcct actttcccta agcgcttgca tcgaaatcga cgtgtttaga     1980
tggggctctg gctccaactc ggtcgagttc gtcgtccctc ctatcgacgc gatcacgtca     2040
caagtcggga cttccgcaac gatcactcag tcgctgtcca atgacctaga tgctggcgtc     2100
gcagcagctc gcgggaaaga tctggctttt gtctttgtca acgcgtgcag tattctaccc     2160
ttcagtcact tttgagacct ttctgacgct gttcttcgat acagtgatag cggggaactg     2220
ggattttaca ctgtcgtcga aggcaacatg ggcgaccgca acgatctgga tctgtggttc     2280
aagggcggta gcttggcacg tcctttttgtt cgttctgaag cgttcagtgt attcatctgc     2340
gttctaggtt gaaggtgttg ccgccgtctg caacaatacg atcgtggtcg tgcactcggt     2400
tggcccagtg agaatgccct ggagcgcgca cccgaatatc acgcgatcg tttatgctgg     2460 cgcgccgggt gagcagaacg ggcctgggct cgttgatgtc ctttatggtg cgtataaccc     2520
gcgcggccgg cttccgttca gcatcagcga tgtaagtttc agcgctttgt ttgcagaatt     2580
caccttgttg atagctctat taggatgagt ccgcgtatag cacatcgatt gtgtacaata     2640
gccttggatt ccccgatgta cgtgccaagt atattcaagt gcatctcgtt tactgattga     2700
cagaccttcg gccccggatt tagatcgact acaccgagaa actgctcctt gactatcgat     2760
```

-continued

```
tcatggacgc gcagaacatc acgccgcgat tcgagttcgg cttcggtctc tcgtacacga    2820
cgttctcgta ctccgacttg atggcgtctg ctacaatcac caacggccag cgggcgctta    2880
cggtgcagtt tacggtggcg aatagcggtt ctgtcgctgg tacagaaatc gcacaggtgt    2940
atcttgggta cccttcgagt gcgggcgagc cgaagagtgt gttgaggggc ttcgatgagg    3000
tagatcttgc ggttggacaa agcaagcaag tacagattgt actgagtcag cgggagctaa    3060
ggtgcgtttt attggagcgg aggatgcacg acgctatgtt tgactgttgc tcgtttagca    3120
tctgggacgt gccgtcgcaa tcgtgggtga taccatcggg tacgtttaca gtccgcgtcg    3180
gtgcctcgat caaggatata cgccttacgg caaccttcta a                        3221
```

<210> SEQ ID NO 8
<211> LENGTH: 740
<212> TYPE: PRT
<213> ORGANISM: Hohenbuehelia mastrucata

<400> SEQUENCE: 8

```
Met Ala Arg Leu Ile Cys Phe Leu Ser Leu Leu Ser Ser Ala Ser Ala
1               5                   10                  15

Phe Thr Leu Arg Ser Trp Thr Asp Ala Tyr Asn Leu Ala Asn Asn Ala
            20                  25                  30

Val Thr Gln Met Thr Leu Asp Glu Lys Val Gly Ile Leu Thr Gly Val
        35                  40                  45

Gly Gln Phe Ser Ser Arg Cys Val Gly Asp Thr His Pro Val Ser Arg
    50                  55                  60

Leu Gly Ile Pro Ser Ile Cys Phe Gln Asp Gly Pro Ala Gly Val Arg
65                  70                  75                  80

Ala Thr Lys Gly Val Thr Gly Phe Pro Thr Gly Ile Asn Thr Ala Ser
                85                  90                  95

Thr Phe Ser Arg Arg Leu Met Arg Ala Arg Gly Val Ala Leu Gly Glu
            100                 105                 110

Glu Phe Arg Gly Lys Gly Ile Asn Val Phe Leu Gly Pro Ala Met Asp
        115                 120                 125

Ile Met Arg Asn Pro Lys Ala Gly Arg Ala Trp Glu Ser Phe Gly Pro
    130                 135                 140

Asp Pro Tyr Leu Asn Gly Glu Gly Ala Phe Glu Thr Ile Thr Gly Val
145                 150                 155                 160

Gln Ser Val Gly Val Gln Ala Cys Ala Lys His Phe Val Gly Asn Asn
                165                 170                 175

Gln Glu His Trp Arg Tyr Gly Ala Ser Ser Asn Ile Asp Asp Arg Thr
            180                 185                 190

Met Asn Glu Ile Tyr Ala Tyr Pro Phe Tyr Arg Ser Ile Asp Ala Gly
        195                 200                 205

Val Thr Ser Ile Met Cys Ala Tyr Asn Arg Val Asn Gly Thr Ser Ser
    210                 215                 220

Cys His Asn Ala Asn Met Leu Gly Asn Gly Leu Leu Arg Lys Asn
225                 230                 235                 240

Gly Phe Met Gly Tyr Val Val Ser Asp Trp Gly Ala Thr His Asp Thr
                245                 250                 255

Ala Ala Asp Asn Ala Asn Ala Gly Leu Glu Met Glu Gln Pro Gly Asp
            260                 265                 270

Phe Ile Val Ile Gly Gly Gly Val Tyr Asn Asn Leu Leu Ser Gly Leu
        275                 280                 285
```

```
Lys Pro Ala Val Asn Ser Gly Lys Val Ser Thr Ala Arg Leu Asn Glu
    290                 295                 300

Met Val Ala Arg Val Leu Ala Gly Trp Tyr Arg Leu Gly Gln Asp Ser
305                 310                 315                 320

Gly Tyr Ala Ala Pro Asn Phe Asp Thr Gln His Ser Asp Gly Ser Gly
                325                 330                 335

Ser Leu Asn Glu Asn Ile Ser Val Arg Ser Asp Ala His Thr Ala Leu
            340                 345                 350

Val Arg Glu Ile Ala Ser Ala Ser Ala Val Leu Leu Lys Asn Asn Arg
        355                 360                 365

Thr Thr Leu Gly Ala Gly Gly Pro Thr Val Arg Gly Leu Pro Val Ala
    370                 375                 380

Gln Ala Gln Val His Ser Met Ala Val Val Gly Leu Asp Ala Met Met
385                 390                 395                 400

Pro Gly Lys Asp Cys Gly Asp Leu Asn Thr Cys Asn Lys Gly Thr Ile
                405                 410                 415

Thr Thr Gly Trp Gly Ser Gly Ser Asn Ser Val Glu Phe Val Val Pro
            420                 425                 430

Pro Ile Asp Ala Ile Thr Ser Gln Val Gly Thr Ser Ala Thr Ile Thr
        435                 440                 445

Gln Ser Leu Ser Asn Asp Leu Asp Ala Gly Val Ala Ala Ala Arg Gly
    450                 455                 460

Lys Asp Leu Ala Phe Val Phe Val Asn Ala Asp Ser Gly Glu Leu Gly
465                 470                 475                 480

Phe Tyr Thr Val Val Glu Gly Asn Met Gly Asp Arg Asn Asp Leu Asp
                485                 490                 495

Leu Trp Phe Lys Gly Gly Ser Leu Ala Arg Pro Phe Val Glu Gly Val
            500                 505                 510

Ala Ala Val Cys Asn Asn Thr Ile Val Val His Ser Val Gly Pro
        515                 520                 525

Val Arg Met Pro Trp Ser Ala His Pro Asn Ile Thr Ala Ile Val Tyr
    530                 535                 540

Ala Gly Ala Pro Gly Glu Gln Asn Gly Pro Gly Leu Val Asp Val Leu
545                 550                 555                 560

Tyr Gly Ala Tyr Asn Pro Arg Gly Arg Leu Pro Phe Ser Ile Ser Asp
                565                 570                 575

Asp Glu Ser Ala Tyr Ser Thr Ser Ile Val Tyr Asn Ser Leu Gly Phe
            580                 585                 590

Pro Asp Ile Asp Tyr Thr Glu Lys Leu Leu Leu Asp Tyr Arg Phe Met
        595                 600                 605

Asp Ala Gln Asn Ile Thr Pro Arg Phe Glu Phe Gly Phe Gly Leu Ser
    610                 615                 620

Tyr Thr Thr Phe Ser Tyr Ser Asp Leu Met Ala Ser Ala Thr Ile Thr
625                 630                 635                 640

Asn Gly Gln Arg Ala Leu Thr Val Gln Phe Thr Val Ala Asn Ser Gly
                645                 650                 655

Ser Val Ala Gly Thr Glu Ile Ala Gln Val Tyr Leu Gly Tyr Pro Ser
            660                 665                 670

Ser Ala Gly Glu Pro Lys Ser Val Leu Arg Gly Phe Asp Glu Val Asp
        675                 680                 685

Leu Ala Val Gly Gln Ser Lys Gln Val Gln Ile Val Leu Ser Gln Arg
    690                 695                 700

Glu Leu Ser Ile Trp Asp Val Pro Ser Gln Ser Trp Val Ile Pro Ser
705                 710                 715                 720
```

Gly Thr Phe Thr Val Arg Val Gly Ala Ser Ile Lys Asp Ile Arg Leu
            725                 730                 735

Thr Ala Thr Phe
            740

<210> SEQ ID NO 9
<211> LENGTH: 3094
<212> TYPE: DNA
<213> ORGANISM: Hohenbuehelia mastrucata

<400> SEQUENCE: 9

| | | | | | |
|---|---|---|---|---|---|
| atggcacgat | tgatctatct | ttcctggctg | gttagcattg | ctagcgcgct | cgagctgcgt | 60 |
| acgcaagcga | tgttatcgat | tttttgcacc | tactcaggct | gaatcttctc | taggtacctg | 120 |
| ggaggatgcg | tatgctctgg | ccaacaatac | agtcagtcag | atgactctcg | atgagaaaat | 180 |
| cgggatcgtt | tctggcgtcg | gaatattcaa | gagtacgtcg | aacttcattc | tggatggcaa | 240 |
| tcgtggcctt | acgcgtcatc | atcttaggtc | gttgctctgg | ggatacacat | cctgttgaac | 300 |
| aatttggtat | ccctccttc | tgctcgttga | atggacccgc | cggagtaggg | gctacattgg | 360 |
| gggtcacagg | cttctcagct | tccattaacg | ttgcatcgac | tttcagtagg | cgtctcatgc | 420 |
| gagcacaagg | cattgcaatt | ggcgaggaaa | cacgaggaaa | gggtgcccag | tatgtgtgat | 480 |
| ttatgcgata | cattccagtt | caagctaatg | aggactacag | cgtcctcctt | gggcctgcaa | 540 |
| tggacatcgt | gagtagtatt | actcctgtct | gattttttt | tcatctataa | taatcattac | 600 |
| gcctagatgc | gcaacccgaa | agccggcagg | tcttgggaag | ggtgagtgga | tcgcatttct | 660 |
| acttgagact | atcggcgagg | ttcaacttct | gacttttgtc | attttttcgtt | ggtctggggt | 720 |
| accgacgttc | actaactaac | gacatatctt | atttctgttg | tatagatatg | gcccggagcc | 780 |
| ctacctgtcg | ggagaagctg | ctttcgaaac | gattactggc | attcagagtg | tcggtgttca | 840 |
| ggcctgtgct | aagcacttca | ttggattcaa | ccaggtgtcg | tggcgaggtg | gtgtatccgt | 900 |
| taccatcgac | gatcggacca | tgcacgaagt | ctatgcgtat | ccattcttcc | ggagtatcga | 960 |
| tgtgagtttc | atcgcgcagc | gaggtatgtt | atcgctcagc | tttgttatgt | gcaggctggg | 1020 |
| gttgcctctg | tcatgtgctc | ctacaaccgt | gtcaataaca | cgcctgcatg | ctcgaacgaa | 1080 |
| aacacgttag | gaaacaatgg | tatcctccgt | aaaaatgggt | tcaaaggtat | ggctttcacg | 1140 |
| tagcttctcg | tctccattcc | tgaccttcga | gtttctcacc | tgttgttagg | ttatatcatg | 1200 |
| agcgactggg | ctgcttcgca | cgggctagcc | aaagacaacg | ccaatgcggg | cctcgacatg | 1260 |
| gagcaacccg | gcgatttgct | tgaaaatgga | ggaggcctat | tcctgaacga | aactgccggc | 1320 |
| ttgaaggcat | ctgtgaacga | tggtaccgtc | tcgaatgaag | tatgtccatg | acgtgccttt | 1380 |
| cgaaagcctt | gctgacctct | agttcagcga | ctggacgaga | tggtctcgcg | cgtcctcgcc | 1440 |
| gcttggtacc | gccttggcca | agaccaagtc | tgtcgtccac | ttcgtcccgg | tttcttcctc | 1500 |
| ctgaagtgta | atcacagggc | tacccacctc | cgaatatcga | tgcgcagaag | cctgatgggt | 1560 |
| ccggcccact | caatctaaat | gtctccgtgc | acacagacgc | acacgtcgcg | ctcgcgcgtg | 1620 |
| aaatttcttc | tgcatcggca | gttctgctga | aaaataatca | gacctcattt | gaggctagag | 1680 |
| aagcaagcat | ccgtggtctt | cctcttgtga | atcgaaaac | tacaagcatg | gcgatcatcg | 1740 |
| ggttagatgc | gaagatgccg | aataagacct | gcgaccagtt | tactgcttgt | aatgatggga | 1800 |
| cagtatccat | agggtacgtc | gtgcattgaa | atgtggtcga | tgttgaccct | gatcatggaa | 1860 |
| tgggatatag | ctatggctca | ggccaaaact | ctctggaatt | caccgttcca | ccgattgacg | 1920 |
| ctatcgttga | ctacgtcggc | aacaattcag | atgttacgca | atctttatcg | aacgacgtgg | 1980 |

```
cagctggtgt tgaatctgcg cgaggcaaag atgtggcatt agtattggtg aacgcgtatg    2040
cgttattccc tccaacttcg cattttttatc agctgacaag tttgtcattg aatagcatca   2100
gtggagaaat gagtatgttt tcgaatggaa ccgagaccgg agatcgttat gacctcgaac    2160
tctggtacga cggagctaag ctagtcagta atccccaacc ctattttcat atccgactga    2220
ttgaatcggt gtcactctag atcgaaggag tcgctgcagt ttgccacaat acgatcgtca    2280
tcgttcactc ggttgggcct gttctaatgc cttggagcaa ccacccgaat atcagtgcaa    2340
tcgtgtatgc tggcgctcca ggtgaacaaa ctggacctgg tcttgtggac gtgctttatg    2400
ggcacgtcaa cccacacggg cgcctcccct tcagcattgc cgacgtatgt tgcctcccaa    2460
atacattgac aaaactaacg ctatccttga acagtccga atcagcgtat ggcaccaaaa     2520
tcgcctacaa tgtcacagga aacgtcgagg tcagttccct cgatatccgt tctgacagtt    2580
tcagggtgaa catgccatat gcaggtggag tacatagaac gacttctgct cgattaccgc    2640
tacatggacg caaagaatat caccccacgc ttcgaatttg gcttcggtct ctcatacacc    2700
acatttgcgt attccgatct ggccatgacg gcaacttcgc ccagtggggt atctatgaac    2760
ttcacggtca agaatacggg agctctcgcg ggcacagaga tccctcagat ctacctctct    2820
taccccgaag ccgccggaga gcctaaaaag gtcctgcgag gcttcgaaga ggtcgaactc    2880
gggccaggag agagcaagga agttgatata accctcagtg agaggagat  caggcatgta    2940 ctgcaagtat cccttagagc atttatgctg acgaacgtgg tgtagtgtat gggacgtcgt    3000
gtcgcaatct tgggttcgtc cgtcaggcac gtacaccgtg cttgtcggtg catccagcaa    3060
ggacattcgg ctcaatacga cttttcgtct ttga                                3094
```

<210> SEQ ID NO 10
<211> LENGTH: 734
<212> TYPE: PRT
<213> ORGANISM: Hohenbuehelia mastrucata

<400> SEQUENCE: 10

```
Met Ala Arg Leu Ile Tyr Leu Ser Trp Leu Val Ser Ile Ala Ser Ala
1               5                   10                  15

Leu Glu Leu Arg Thr Trp Glu Asp Ala Tyr Ala Leu Ala Asn Asn Thr
            20                  25                  30

Val Ser Gln Met Thr Leu Asp Glu Lys Ile Gly Ile Ser Gly Val
        35                  40                  45

Gly Ile Phe Lys Ser Arg Cys Ser Gly Asp Thr His Pro Val Glu Gln
    50                  55                  60

Phe Gly Ile Pro Ser Phe Cys Ser Leu Asn Gly Pro Ala Gly Val Gly
65                  70                  75                  80

Ala Thr Leu Gly Val Thr Gly Phe Ser Ala Ser Ile Asn Val Ala Ser
                85                  90                  95

Thr Phe Ser Arg Arg Leu Met Arg Ala Gln Gly Ile Ala Ile Gly Glu
            100                 105                 110

Glu Thr Arg Gly Lys Gly Ala His Val Leu Leu Gly Pro Ala Met Asp
        115                 120                 125

Ile Met Arg Asn Pro Lys Ala Gly Arg Ser Trp Glu Gly Tyr Gly Pro
    130                 135                 140

Glu Pro Tyr Leu Ser Gly Glu Ala Ala Phe Glu Thr Ile Thr Gly Ile
145                 150                 155                 160

Gln Ser Val Gly Val Gln Ala Cys Ala Lys His Phe Ile Gly Phe Asn
                165                 170                 175
```

-continued

```
Gln Val Ser Trp Arg Gly Gly Val Ser Val Thr Ile Asp Asp Arg Thr
            180                 185                 190

Met His Glu Val Tyr Ala Tyr Pro Phe Phe Arg Ser Ile Asp Ala Gly
            195                 200                 205

Val Ala Ser Val Met Cys Ser Tyr Asn Arg Val Asn Asn Thr Pro Ala
            210                 215                 220

Cys Ser Asn Glu Asn Thr Leu Gly Asn Gly Ile Leu Arg Lys Asn
225                 230                 235                 240

Gly Phe Lys Gly Tyr Ile Met Ser Asp Trp Ala Ser His Gly Leu
            245                 250                 255

Ala Lys Asp Asn Ala Asn Ala Gly Leu Asp Met Glu Gln Pro Gly Asp
            260                 265                 270

Leu Leu Glu Asn Gly Gly Gly Leu Phe Leu Asn Glu Thr Ala Gly Leu
            275                 280                 285

Lys Ala Ser Val Asn Asp Gly Thr Val Ser Asn Glu Arg Leu Asp Glu
            290                 295                 300

Met Val Ser Arg Val Leu Ala Ala Trp Tyr Arg Leu Gly Gln Asp Gln
305                 310                 315                 320

Gly Tyr Pro Pro Asn Ile Asp Ala Gln Lys Pro Asp Gly Ser Gly
            325                 330                 335

Pro Leu Asn Leu Asn Val Ser Val His Thr Asp Ala His Val Ala Leu
            340                 345                 350

Ala Arg Glu Ile Ser Ser Ala Ser Ala Val Leu Leu Lys Asn Asn Gln
            355                 360                 365

Thr Ser Phe Glu Ala Arg Glu Ala Ser Ile Arg Gly Leu Pro Leu Val
            370                 375                 380

Lys Ser Lys Thr Thr Ser Met Ala Ile Ile Gly Leu Asp Ala Lys Met
385                 390                 395                 400

Pro Asn Lys Thr Cys Asp Gln Phe Thr Ala Cys Asn Asp Gly Thr Val
            405                 410                 415

Ser Ile Gly Tyr Gly Ser Gly Gln Asn Ser Leu Glu Phe Thr Val Pro
            420                 425                 430

Pro Ile Asp Ala Ile Val Asp Tyr Val Gly Asn Asn Ser Asp Val Thr
            435                 440                 445

Gln Ser Leu Ser Asn Asp Val Ala Ala Gly Val Glu Ser Ala Arg Gly
            450                 455                 460

Lys Asp Val Ala Leu Val Leu Val Asn Ala Ile Ser Gly Glu Met Ser
465                 470                 475                 480

Met Phe Ser Asn Gly Thr Glu Thr Gly Asp Arg Tyr Asp Leu Glu Leu
            485                 490                 495

Trp Tyr Asp Gly Ala Lys Leu Ile Glu Gly Val Ala Ala Val Cys His
            500                 505                 510

Asn Thr Ile Val Ile Val His Ser Val Gly Pro Val Leu Met Pro Trp
            515                 520                 525

Ser Asn His Pro Asn Ile Ser Ala Ile Val Tyr Ala Gly Ala Pro Gly
            530                 535                 540

Glu Gln Thr Gly Pro Gly Leu Val Asp Val Leu Tyr Gly His Val Asn
545                 550                 555                 560

Pro His Gly Arg Leu Pro Phe Ser Ile Ala Asp Ser Glu Ser Ala Tyr
            565                 570                 575

Gly Thr Lys Ile Ala Tyr Asn Val Thr Gly Asn Val Glu Val Glu Tyr
            580                 585                 590

Ile Glu Arg Leu Leu Leu Asp Tyr Arg Tyr Met Asp Ala Lys Asn Ile
            595                 600                 605
```

```
Thr Pro Arg Phe Glu Phe Gly Phe Gly Leu Ser Tyr Thr Thr Phe Ala
    610                 615                 620
Tyr Ser Asp Leu Ala Met Thr Ala Thr Ser Pro Ser Gly Val Ser Met
625                 630                 635                 640
Asn Phe Thr Val Lys Asn Thr Gly Ala Leu Ala Gly Thr Glu Ile Pro
                645                 650                 655
Gln Ile Tyr Leu Ser Tyr Pro Glu Ala Ala Gly Glu Pro Lys Lys Val
            660                 665                 670
Leu Arg Gly Phe Glu Glu Val Glu Leu Gly Pro Gly Glu Ser Lys Glu
        675                 680                 685
Val Asp Ile Thr Leu Ser Glu Arg Glu Ile Ser Val Trp Asp Val Val
    690                 695                 700
Ser Gln Ser Trp Val Arg Pro Ser Gly Thr Tyr Thr Val Leu Val Gly
705                 710                 715                 720
Ala Ser Ser Lys Asp Ile Arg Leu Asn Thr Thr Phe Arg Leu
                725                 730

<210> SEQ ID NO 11
<211> LENGTH: 3600
<212> TYPE: DNA
<213> ORGANISM: Hohenbuehelia mastrucata

<400> SEQUENCE: 11
atggccaagc ttacacccct tgctccttgcc ctcagtttaa cggtctgttg cagcggacta      60
agctccagta accatgtcgc gagtacgtcc gcgccgaaag cttctgatgt tgcttcgtcg     120
acgatccacc gggccactat agtcccttct tcgggctcat caacggtgag gctcacgaca     180
ggttcgacgg ttacagggac agctgcaagc tctccattat tgctctctct cccgacatcc     240
gcgccaagta ccctatctgc aagcggcgcc tcggcgattg ccacttctgg attcggctct     300
actatagcca gcggaagtat tccccagagt gttccctcgc aggcgccagt tgcaggggtg     360
tttccagcca ccaaccccaa gcagccgcct tcttttcagc agagcggaaa agtcatacct     420
gattttgggc cggcatgggc agatgctatt gcgaaggcaa aggctaaagt gagtttaaga     480
tttagccaca tcaaatacat acattaaatt atctccctgt agattgcagg gttcagtgtt     540
gaggagctcg ctgcagtaac tacgggtcaa gaaagcactg gcgtatcggg agatgtgta     600
ggaaatattc ctccaatcgg ttcggcgtca aaaggctggt ctggtttatg tctgcaggta     660
tgcgggattg gcatcgggaa tatgacatac taactcaaac gaatttcgaa ggactcgccc     720
cttggggtgc gtttagcgga cttttgtgacc gctttccccg ctggaattaa cacagcagca     780
acgtgagtaa cgctcgtggt caagaaataa agacagatta cctgtgacca aatcacaccc     840
ttaacaggtt caatcgaggc ctgattcgcc agcgtggatt attcatggga atggaacacg     900
tagggaaagg cgtgaatgtt gctctcggac ccatgatgaa tcttggtagg gtagcggaag     960
ccggtagaaa ttttgaagga tttggttcgg atcctttctt ggctggtgaa ggtacgctct    1020
ccgcgctctc tctgggtcct aagaaattgg acggcatact tatactcctt gaaacgaaag    1080
ctgcgtacga gacgattctt ggaatgcaac aaggcggcgt ccaggcgtgt gcaaagcatt    1140
acattgacaa gtaggctcat tgcatactgt gcgtcgtgtc ttgccgctga tataccgcta    1200
agcgagcaag aaacagcacg tacgacctca tcttcaatcg tcgacgatcg cacacaacac    1260
gaggtgtatg ctctgccgtt catccggagc gtcatggctg gtgtagccag catcatgtgc    1320
agctacagtg agaatcccac ccgtgaccca tttacaaccc tgatgtacat tcggtaatag    1380
atcagataaa cggaacgtat gcctgcgaga tgaaaaaact gctgaatggg gttctgaaaa    1440
```

```
cggagatagg gttttctggg tgtgagtctt gatttctcat tttagatgga tacttagcta   1500
aacatgtgta ttacaagacg ttatgtctga ctgggggggct actcattcaa cattatcagc   1560
cgcaacagga cttgatgtac gtgttccgag aaatttaagt tatagaccac ggattttgat   1620
gcggggttaa caaaacgcac agatgacaat gccgggtaat attgggcgcg gaccgggatc   1680
gtattttgga ggaaacctaa cagcgtttgt ccaaaatggc accatatcca aggcgcgctt   1740
ggaagatatg gcggtcagca ttcttaggct gcttgagggt tacgtcgtat aaatgctaac   1800 ttccttgatct gtgaaagact cgcatcctcg ctggatggta cctcctcaat caagactcgc   1860
cctcttaccc taccgtaaat ttcaacggaa acaaccctgc agaggaggca acaaacgagc   1920
acatcgacgt tcaagacgat catcataccg tcgtccgcga tatcggggct gcgagcatcg   1980
ttttactgaa gaacgaggga ggtgctctgc ctttgaagaa gccaagaagt cttctgcttg   2040
ctggcagtga cgccggtcca gggcgcattg gaccgaacga gttcagagac cagacgggga   2100
acgatggcat tttggccatg gggtggggct ctggtgcgtt ttatattcag cttcgtagtt   2160
gaactggtaa ttgagctggc tccgtacagc actgcgaact ttacatacct aatttcggta   2220
aggtcaccca caaagtatt gaacgctact cagcctgtga tgccattgca gcctctagaa   2280
gctattcagc ggcgagcgcg ccaggatagg acatcgatgt cctggacctt gaacgatttt   2340
gatctccctc cgcagggcaa tatggccatt ggccgttcag ccacactggt gtttgtcaat   2400
gctgactctg gggagggaag cgacaggtct gcacgttggc aaatttgcga gatcttgggc   2460
tgattttgtg ctccttagga cgaatctcac gacttggcat ggaggcgagg accttattct   2520
cgcagtggcc gctcagaaca caacacgat cgtggtcgtg catagcgtcg gccaggtaat   2580
cgtcgagagc tggattgacc atcccaacgt caccgccgtg agttatcgcg tccggaattt   2640
tctcgtacct tcgtgcattc atgtgtgcct gtacaaggtt ttatgggcag gtgtatcagg   2700
aaccgagact ggcaacgcat tgaccgatgt cctgtacggc gacgtgaacc cctcggggcg   2760
gcttccctac acaatcgcaa aacggccaga ggactatccc gcgcaagtga taccgaacac   2820
cccagggcag attgtccaag taccttatac ggatgggcaa gtactctgcg gtgcggataa   2880
gaatgcgtgg aaggctgatg aaatactact ataacaggct cttcattgac taccggtcat   2940
tcgacgcggt aagctgaaca aaactcgtgt caggagaata tgctcacgga tcctcagaga   3000
aatatcactc cgcgcttcga gttcggcttc ggtttgagtt atacgaagtt tgcctatagc   3060
aacctccgta tctcgaaggt ctctagtcct gatggagcac aggcagctct agaaagaaac   3120
tgggaggcgg gtaggccgag tccgactggt gttggatctt ccacggcgct gtggtaagcc   3180
atagtcgctt gacatagcaa ctgtgcaggc gctgacagtc aaaattaggt tgcatcgctc   3240
ggcattcaag gtcactttcg atgtccaaaa tattggatcg gtagctggta ccgaggtgtg   3300
tcaattctag atctcttgcc caaatttatc gagaaactct cttacggctg cgagcagatt   3360
ccccagctct acgtgcgcct gccaccgtct gctgaagagc cgccgtcaat tttgaaagga   3420
tttgacaacg tatcgctgaa gcctaaggaa acgcaaacag tttctatcac gctttcacgc   3480
catgcgttat ccgtgtggga cgtcgttggt caagggtgga aaaggccaca aggcgaaata   3540
ggcatcctga taggggcgag cagccgcgac cttcgactac atgggagct tccgttatga   3600
```

<210> SEQ ID NO 12
<211> LENGTH: 882
<212> TYPE: PRT
<213> ORGANISM: Hohenbuehelia mastrucata

<400> SEQUENCE: 12

```
Met Ala Lys Leu Thr Pro Leu Leu Ala Leu Ser Leu Thr Val Cys
1               5                   10                  15

Cys Ser Gly Leu Ser Ser Asn His Val Ala Ser Thr Ser Ala Pro
            20              25                  30

Lys Ala Ser Asp Val Ala Ser Thr Ile His Arg Ala Thr Ile Val
        35                  40                  45

Pro Ser Ser Gly Ser Ser Thr Val Arg Leu Thr Thr Gly Ser Thr Val
    50                  55                  60

Thr Gly Thr Ala Ala Ser Ser Pro Leu Leu Leu Ser Leu Pro Thr Ser
65                  70                  75                  80

Ala Pro Ser Thr Leu Ser Ala Ser Gly Ala Ser Ala Ile Ala Thr Ser
                85                  90                  95

Gly Phe Gly Ser Thr Ile Ala Ser Gly Ser Ile Pro Gln Ser Val Pro
                100                 105                 110

Ser Gln Ala Pro Val Ala Gly Val Phe Pro Ala Thr Asn Pro Lys Gln
        115                 120                 125

Pro Pro Ser Phe Gln Gln Ser Gly Lys Val Ile Pro Asp Phe Gly Pro
    130                 135                 140

Ala Trp Ala Asp Ala Ile Ala Lys Ala Lys Ala Lys Ile Ala Gly Phe
145                 150                 155                 160

Ser Val Glu Glu Leu Ala Ala Val Thr Thr Gly Gln Glu Ser Thr Gly
                165                 170                 175

Val Ser Gly Arg Cys Val Gly Asn Ile Pro Pro Ile Gly Ser Ala Ser
                180                 185                 190

Lys Gly Trp Ser Gly Leu Cys Leu Gln Asp Ser Pro Leu Gly Val Arg
        195                 200                 205

Leu Ala Asp Phe Val Thr Ala Phe Pro Ala Gly Ile Asn Thr Ala Ala
    210                 215                 220

Thr Phe Asn Arg Gly Leu Ile Arg Gln Arg Gly Leu Phe Met Gly Met
225                 230                 235                 240

Glu His Val Gly Lys Gly Val Asn Val Ala Leu Gly Pro Met Met Asn
                245                 250                 255

Leu Gly Arg Val Ala Glu Ala Gly Arg Asn Phe Glu Gly Phe Gly Ser
            260                 265                 270

Asp Pro Phe Leu Ala Gly Glu Ala Ala Tyr Glu Thr Ile Leu Gly Met
        275                 280                 285

Gln Gln Gly Gly Val Gln Ala Cys Ala Lys His Tyr Ile Asp Asn Glu
    290                 295                 300

Gln Glu Thr Ala Arg Thr Thr Ser Ser Ser Ile Val Asp Asp Arg Thr
305                 310                 315                 320

Gln His Glu Val Tyr Ala Leu Pro Phe Ile Arg Ser Val Met Ala Gly
                325                 330                 335

Val Ala Ser Ile Met Cys Ser Tyr Asn Gln Ile Asn Gly Thr Tyr Ala
            340                 345                 350

Cys Glu Asn Glu Lys Leu Leu Asn Gly Val Leu Lys Thr Glu Ile Gly
        355                 360                 365

Phe Ser Gly Tyr Val Met Ser Asp Trp Gly Ala Thr His Ser Thr Leu
    370                 375                 380

Ser Ala Ala Thr Gly Leu Asp Met Thr Met Pro Gly Asn Ile Gly Arg
385                 390                 395                 400

Gly Pro Gly Ser Tyr Phe Gly Gly Asn Leu Thr Ala Phe Val Gln Asn
                405                 410                 415
```

```
Gly Thr Ile Ser Lys Ala Arg Leu Glu Asp Met Ala Thr Arg Ile Leu
            420                 425                 430

Ala Gly Trp Tyr Leu Leu Asn Gln Asp Ser Pro Ser Tyr Pro Thr Val
        435                 440                 445

Asn Phe Asn Gly Asn Asn Pro Ala Glu Ala Thr Asn Glu His Ile
450                 455                 460

Asp Val Gln Asp Asp His His Thr Val Val Arg Asp Ile Gly Ala Ala
465                 470                 475                 480

Ser Ile Val Leu Leu Lys Asn Glu Gly Ala Leu Pro Leu Lys Lys
                485                 490                 495

Pro Arg Ser Leu Leu Ala Gly Ser Asp Ala Gly Pro Gly Arg Ile
            500                 505                 510

Gly Pro Asn Glu Phe Arg Asp Gln Thr Gly Asn Asp Gly Ile Leu Ala
        515                 520                 525

Met Gly Trp Gly Ser Gly Thr Ala Asn Phe Thr Tyr Leu Ile Ser Pro
        530                 535                 540

Leu Glu Ala Ile Gln Arg Arg Ala Arg Gln Asp Arg Thr Ser Met Ser
545                 550                 555                 560

Trp Thr Leu Asn Asp Phe Asp Leu Pro Arg Ala Gly Asn Met Ala Ile
                565                 570                 575

Gly Arg Ser Ala Thr Leu Val Phe Val Asn Ala Asp Ser Gly Glu Gly
            580                 585                 590

Ser Asp Arg Thr Asn Leu Thr Thr Trp His Gly Gly Glu Asp Leu Ile
        595                 600                 605

Leu Ala Val Ala Ala Gln Asn Asn Asn Thr Ile Val Val Val His Ser
        610                 615                 620

Val Gly Gln Val Ile Val Glu Ser Trp Ile Asp His Pro Asn Val Thr
625                 630                 635                 640

Ala Val Leu Trp Ala Gly Val Ser Gly Thr Glu Thr Gly Asn Ala Leu
                645                 650                 655

Thr Asp Val Leu Tyr Gly Asp Val Asn Pro Ser Gly Arg Leu Pro Tyr
            660                 665                 670

Thr Ile Ala Lys Arg Pro Glu Asp Tyr Pro Ala Gln Val Ile Pro Asn
        675                 680                 685

Thr Pro Gly Gln Ile Val Gln Val Pro Tyr Thr Asp Gly Gln Val Leu
690                 695                 700

Cys Gly Ala Asp Lys Asn Ala Leu Phe Ile Asp Tyr Arg Ser Phe Asp
705                 710                 715                 720

Ala Arg Asn Ile Thr Pro Arg Phe Glu Phe Gly Phe Gly Leu Ser Tyr
                725                 730                 735

Thr Lys Phe Ala Tyr Ser Asn Leu Arg Ile Ser Lys Val Ser Ser Pro
            740                 745                 750

Asp Gly Ala Gln Ala Ala Leu Glu Arg Asn Trp Glu Ala Gly Arg Pro
        755                 760                 765

Ser Pro Thr Gly Val Gly Ser Ser Thr Ala Leu Trp Leu His Arg Ser
        770                 775                 780

Ala Phe Lys Val Thr Phe Asp Val Gln Asn Ile Gly Ser Val Ala Gly
785                 790                 795                 800

Thr Glu Ile Pro Gln Leu Tyr Val Arg Leu Pro Pro Ser Ala Glu Glu
                805                 810                 815

Pro Pro Ser Ile Leu Lys Gly Phe Asp Asn Val Ser Leu Lys Pro Lys
            820                 825                 830

Glu Thr Gln Thr Val Ser Ile Thr Leu Ser Arg His Ala Leu Ser Val
        835                 840                 845
```

Trp Asp Val Val Gly Gln Gly Trp Lys Arg Pro Gln Gly Glu Ile Gly
    850             855             860

Ile Leu Ile Gly Ala Ser Ser Arg Asp Leu Arg Leu His Gly Glu Leu
865             870             875             880

Pro Leu

<210> SEQ ID NO 13
<211> LENGTH: 48
<212> TYPE: DNA
<213> ORGANISM: Artificial
<220> FEATURE:
<223> OTHER INFORMATION: PCR primer

<400> SEQUENCE: 13
acacaactgg ggatccacca tgtctcggtt attcgccaga gtcgctct            48

<210> SEQ ID NO 14
<211> LENGTH: 43
<212> TYPE: DNA
<213> ORGANISM: Artificial
<220> FEATURE:
<223> OTHER INFORMATION: PCR primer

<400> SEQUENCE: 14
agatctcgag aagcttattt cggcgatggg gtcgaagttg agt                 43

<210> SEQ ID NO 15
<211> LENGTH: 52
<212> TYPE: DNA
<213> ORGANISM: Artificial
<220> FEATURE:
<223> OTHER INFORMATION: PCR primer

<400> SEQUENCE: 15
acacaactgg ggatccacca tgagagggct actgtctttt acgctccttt ca       52

<210> SEQ ID NO 16
<211> LENGTH: 42
<212> TYPE: DNA
<213> ORGANISM: Artificial
<220> FEATURE:
<223> OTHER INFORMATION: PCR primer

<400> SEQUENCE: 16
agatctcgag aagcttatgt aaccgtcagc gtcgcattcg ca                  42

<210> SEQ ID NO 17
<211> LENGTH: 41
<212> TYPE: DNA
<213> ORGANISM: Artificial
<220> FEATURE:
<223> OTHER INFORMATION: PCR primer

<400> SEQUENCE: 17
acacaactgg ggatccacca tggccaccct caccctgctc a                   41

<210> SEQ ID NO 18
<211> LENGTH: 48
<212> TYPE: DNA
<213> ORGANISM: Artificial
<220> FEATURE:
<223> OTHER INFORMATION: PCR primer

<400> SEQUENCE: 18
agatctcgag aagcttaaac aggaatgctg cccttcagcc tgaaatcc            48

<210> SEQ ID NO 19
<211> LENGTH: 50
<212> TYPE: DNA
<213> ORGANISM: Artificial
<220> FEATURE:
<223> OTHER INFORMATION: PCR primer

<400> SEQUENCE: 19
acacaactgg ggatccacca tggctcgctt gatctgcttc ctctctttgc       50

<210> SEQ ID NO 20
<211> LENGTH: 50
<212> TYPE: DNA
<213> ORGANISM: Artificial
<220> FEATURE:
<223> OTHER INFORMATION: PCR primer

<400> SEQUENCE: 20
agatctcgag aagcttagaa ggttgccgta aggcgtatat ccttgatcga       50

<210> SEQ ID NO 21
<211> LENGTH: 51
<212> TYPE: DNA
<213> ORGANISM: Artificial
<220> FEATURE:
<223> OTHER INFORMATION: PCR primer

<400> SEQUENCE: 21
acacaactgg ggatccacca tggcacgatt gatctatctt tcctggctgg t     51

<210> SEQ ID NO 22
<211> LENGTH: 52
<212> TYPE: DNA
<213> ORGANISM: Artificial
<220> FEATURE:
<223> OTHER INFORMATION: PCR primer

<400> SEQUENCE: 22
agatctcgag aagcttaaag acgaaaagtc gtattgagcc gaatgtcctt gc    52

<210> SEQ ID NO 23
<211> LENGTH: 45
<212> TYPE: DNA
<213> ORGANISM: Artificial
<220> FEATURE:
<223> OTHER INFORMATION: PCR primer

<400> SEQUENCE: 23
acacaactgg ggatccacca tggccaagct tacacccttg ctcct            45

<210> SEQ ID NO 24
<211> LENGTH: 46
<212> TYPE: DNA
<213> ORGANISM: Artificial
<220> FEATURE:
<223> OTHER INFORMATION: PCR primer

<400> SEQUENCE: 24
agatctcgag aagcttataa cggaagctcc ccatgtagtc gaaggt           46

POLYPEPTIDES HAVING BETA-GLUCOSIDASE AND BETA-XYLOSIDASE ACTIVITY AND POLYNUCLEOTIDES ENCODING SAME

CROSS-REFERENCE TO RELATED APPLICATIONS

This application claims priority or the benefit under 35 U.S.C. 119 of U.S. provisional application No. 61/561,446 filed on Nov. 18, 2011, the contents of which are fully incorporated herein by reference.

REFERENCE TO A SEQUENCE LISTING

This application contains a Sequence Listing in computer readable form, which is incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

BACKGROUND OF THE INVENTION

1. Field of the Invention

The present invention relates to polypeptides having beta-glucosidase activity, beta-xylosidase activity, or beta-glucosidase and beta-xylosidase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

There is a need in the art for polypeptides having beta-glucosidase activity, beta-xylosidase activity, or beta-glucosidase and beta-xylosidase activity with improved properties for use in the degradation of cellulosic and xylan-containing materials.

The present invention provides new polypeptides having beta-glucosidase activity, beta-xylosidase activity, or beta-glucosidase and beta-xylosidase activity and polynucleotides encoding the polypeptides.

The polypeptides according to the invention share 63.29% identity (excluding gaps) to the deduced amino acid sequence of a GH3 family protein from *Moniliophtora perniciosa* (SwissProt accession number E2LXM8), 69.97% identity (excluding gaps) to the deduced amino acid sequence of a GH3 family protein from *Postia placenta* (SwissProt accession number B8P3Z6), 75.92% identity (excluding gaps) to the deduced amino acid sequence of a GH3 family protein from *Laccaria bicolor* (SwissProt accession number 0D734), 72.66% identity (excluding gaps) to the deduced amino acid sequence of a GH3 family protein from *Laccaria bicolor* (SwissProt accession number B0D3B6), 61.71% identity (excluding gaps) to the deduced amino acid sequence of a GH3 family protein from *Laccaria bicolor* (SwissProt accession number B0D3B6), 68.90% identity (excluding gaps) to the deduced amino acid sequence of a GH3 family protein from *Laccaria bicolor* (SwissProt accession number B0D734) respectively.

SUMMARY OF THE INVENTION

The present invention relates to isolated polypeptides having beta-glucosidase activity, beta-xylosidase activity, or beta-glucosidase and beta-xylosidase activity selected from the group consisting of:

(a) a polypeptide having at least 76% sequence identity to the mature polypeptide of SEQ ID NO: 2, SEQ ID NO: 4, SEQ ID NO: 6, SEQ ID NO: 8, SEQ ID NO: 10, or SEQ ID NO: 12;

(b) a polypeptide encoded by a polynucleotide that hybridizes under at least midium stringency conditions with (i) the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, or the mature polypeptide coding sequence of SEQ ID NO: 11 or the cDNA sequence thereof, or (ii) the full-length complement of (i);

(c) a polypeptide encoded by a polynucleotide having at least 76% sequence identity to the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, or the mature polypeptide coding sequence of SEQ ID NO: 11 or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions; and (e) a fragment of the polypeptide of (a), (b), (c), or (d) that has beta-glucosidase activity, beta-xylosidase activity, or beta-glucosidase and beta-xylosidase activity.

The present invention also relates to isolated polynucleotides encoding the polypeptides of the present invention, nucleic acid constructs, recombinant expression vectors, and recombinant host cells comprising the polynucleotides, and methods of producing the polypeptides.

The present invention also relates to processes for degrading or converting a cellulosic material or xylan-containing material, comprising: treating the cellulosic material or xylan-containing material with an enzyme composition in the presence of a polypeptide having beta-glucosidase activity, beta-xylosidase activity, or beta-glucosidase and beta-xylosidase activity of the present invention.

The present invention also relates to processes of producing a fermentation product, comprising: (a) saccharifying a cellulosic material or xylan-containing material with an enzyme composition in the presence of a polypeptide having beta-glucosidase activity, beta-xylosidase activity, or beta-glucosidase and beta-xylosidase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of the present invention.

The present invention also relates to a polynucleotide encoding a signal peptide comprising or consisting of amino acids 1 to 20 of SEQ ID NO: 2, amino acids 1 to 19 of SEQ ID NO: 4, amino acids 1 to 15 of SEQ ID NO: 6, amino acids 1 to 16 of SEQ ID NO: 8, amino acids 1 to 16 of SEQ ID NO: 10, or amino acids 1 to 23 of SEQ ID NO: 12 which is operably linked to a gene encoding a protein, wherein the gene is foreign to the polynucleotide encoding the signal peptide; nucleic acid constructs, expression vectors, and recombinant host cells comprising the polynucleotides; and methods of producing a protein.

Definitions

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 micromole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 microliters for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 micromole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 micromole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-glucosidase activity of the mature polypeptide of SEQ ID NO: 2, SEQ ID NO: 4, SEQ ID NO: 6, SEQ ID NO: 8, SEQ ID NO: 10, or SEQ ID NO: 12.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 micromole of p-nitrophenolate anion produced per minute at 40° C., pH 5 from 1 mM p-nitrophenyl-beta-D-xyloside as substrate in 100 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-xylosidase activity of the mature polypeptide of SEQ ID NO: 2, SEQ ID NO: 4, SEQ ID NO: 6, or SEQ ID NO: 8, SEQ ID NO: 10, or SEQ ID NO: 12.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-beta-D-lactoside.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., 2006, Outlook for cellulase improvement: Screening and selection strategies, *Biotechnology Advances* 24: 452-481. Total cellulolytic activity is usually measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 micromole of p-nitrophenolate anion per minute at pH 5, 25° C.

Fragment: The term "fragment" means a polypeptide having one or more (e.g., several) amino acids deleted from the amino and/or carboxyl terminus of a mature polypeptide; wherein the fragment has beta-glucosidase activity, beta-xylosidase activity, or beta-glucosidase and beta-xylosidase activity. In one aspect, a fragment contains at least 339 amino acid residues, e.g., amino acid residues 25 to 363 of SEQ ID NO: 2. In another aspect, a fragment contains at least 541 amino acid residues, e.g., at least amino acid residues 199 to 739 of SEQ ID NO: 2. In another aspect, a fragment contains at least 367 amino acids, e.g., amino acids 42 to 408 of SEQ ID NO: 4. In another aspect, a fragment contains at least 324 amino acids, e.g., amino acids 118 to 441 of SEQ ID NO: 6. In another aspect, a fragment contains at least 322 amino acids, e.g., amino acids 17 to 338 of SEQ ID NO:8. In another aspect, a fragment contains at least 318 amino acids, e.g., amino acids 21 to 338 of SEQ ID NO: 10. In another aspect, a fragment contains at least 329 amino acids, e.g., amino acids 138 to 466 of SEQ ID NO: 12.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 774 of SEQ ID NO: 2 based on the SignalP program (Nielsen et al., 1997, *Protein Engineering* 10:1-6) that predicts amino acids 1 to 20 of SEQ ID NO: 2 are a signal peptide. In another aspect, the mature polypeptide is amino acids 20 to 799 of SEQ ID NO: 4 based on the SignalP program that predicts amino acids 1 to 19 of SEQ ID NO: 4 are a signal peptide. In another aspect, the mature polypeptide is amino acids 16 to 858 of SEQ ID NO: 6 based on the SignalP program that predicts amino acids 1 to 15 of SEQ ID NO: 6 are a signal peptide. In another aspect, the mature polypeptide is amino acids 17 to 740 of SEQ ID NO: 8 based on the SignalP program that predicts amino acids 1 to 16 of SEQ ID NO: 8 are a signal peptide. In another aspect, the mature polypeptide is amino acids 17 to 734 of SEQ ID NO: 10 based on the SignalP program that predicts amino acids 1 to 16 of SEQ ID NO: 10 are a signal peptide. In another aspect, the mature polypeptide is amino acids 24 to 882 of SEQ ID NO: 12 based on the SignalP program that predicts amino acids 1 to 23 of SEQ ID NO: 12 are a signal peptide.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having beta-glucosidase activity, beta-xylosidase activity, or beta-glucosidase and beta-xylosidase activity. In one aspect, the mature polypeptide coding sequence is nucleotides 61 to 2490 of SEQ ID NO: 1 based on the SignalP program (Nielsen et al., 1997, supra) that predicts nucleotides 1 to 60 of SEQ ID NO: 1 encode a signal peptide. In another aspect, the mature polypeptide coding sequence is the cDNA sequence contained in nucleotides 61 to 2490 of SEQ ID NO: 1. In another aspect the mature polypeptide coding sequence is nucleotides 61 to 264, 318 to 1129, 1190 to 1736, 1789 to 2490 of SEQ ID NO: 1. In another aspect, the mature polypeptide coding sequence is nucleotides 58 to 3247 of SEQ ID NO: 3 based on the SignalP program that predicts nucleotides 1 to 57 of SEQ ID NO: 3 encode a signal peptide. In another aspect, the mature polypeptide coding sequence is the cDNA sequence contained in nucleotides 58 to 3247 of SEQ ID NO: 3. In another aspect the mature polypeptide coding sequence is nucleotides 58 to 224, 274 to 352, 405 to 549, 613 to 961, 1015 to 1154, 1219 to 1235, 1299 to 1473, 1523 to 1615, 1661 to 1836, 1896 to 2283, 2355 to 2432, 2488 to 2615, 2679 to 2746, 2799 to 2904, 2963 to 3039, 3091 to 3247 of SEQ ID NO: 3. In another aspect, the mature polypeptide coding sequence is nucleotides 46 to 3290 of SEQ ID NO: 5 based on the SignalP program that predicts nucleotides 1 to 45 of SEQ ID NO: 5 encode a signal peptide. In another aspect, the mature polypeptide coding sequence is the cDNA sequence contained in nucleotides 46 to 3290 of SEQ ID NO: 5. In another aspect the mature polypeptide coding sequence is nucleotides 46 to 408, 457 to 644, 699 to 835, 893 to 919, 970 to 1039, 1093 to 1217, 1272 to 1352, 1409 to 1467, 1518 to 1628, 1679 to 2029, 2083 to 2261, 2322 to 2676, 2738 to 2980, 3048 to 3290 of SEQ ID NO: 5. In another aspect, the mature polypeptide coding sequence is nucleotides 49 to 3221 of SEQ ID NO: 7 based on the SignalP program that predicts nucleotides 1 to 48 of SEQ ID NO: 7 encode a signal peptide. In another aspect, the mature polypeptide coding sequence is the cDNA sequence contained in nucleotides 49 to of 3221 SEQ ID NO: 7. In another aspect the mature polypeptide coding sequence is nucleotides 49 to 58, 108 to 206, 265 to 466, 523 to 550, 606 to 640, 857 to 1052, 1109 to 1220, 1275 to 1444, 1508 to 1567, 1631 to 1926, 1980 to 2144, 2205 to 2307, 2348 to 2551, 2604 to 2657, 2724 to 3061, 3119 to 3221 of SEQ ID NO: 7. In another aspect, the mature polypeptide coding sequence is nucleotides 49 to 3094 of SEQ ID NO: 9 based on the SignalP program that predicts nucleotides 1 to 48 of SEQ ID NO: 9 encode a signal peptide. In another aspect, the mature polypeptide coding sequence is the cDNA sequence contained in nucleotides 49 to 3094 of SEQ ID NO: 9. In another aspect the mature polypeptide coding sequence is nucleotides 49 to 58, 114 to 212, 268 to 469, 521 to 548, 607 to 641, 766 to 961, 1015 to 1126, 1190 to 1359, 1408 to 1467, 1518 to 1813, 1871 to 2035, 2096 to 2183, 2241 to 2444, 2496 to 2549, 2605 to 2933, 2986 to 3094 of SEQ ID NO: 9. In another aspect, the mature polypeptide coding sequence is nucleotides 70 to 3600 of SEQ ID NO: 11 based on the SignalP program that predicts nucleotides 1 to 69 of SEQ ID NO: 11 encode a signal peptide. In another aspect, the mature polypeptide coding sequence is the cDNA sequence contained in nucleotides 70 to 3600 of SEQ ID NO: 11. In another aspect the mature polypeptide coding sequence is nucleotides 70 to 468, 523 to 657, 712 to 782, 848 to 1011, 1081 to 1150, 1203 to 1327, 1381 to 1461, 1518 to 1576, 1643 to 1753, 1818 to 2134, 2190 to 2217, 2272 to 2426, 2479 to 2617, 2678 to 2886, 2918 to 2948, 2998 to 3173, 3229 to 3295, 3358 to 3600 of SEQ ID NO: 11.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight Aspergillus oryzae beta-glucosidase (recombinantly produced in Aspergillus oryzae according to WO 02/095014) or 2-3% of total protein weight Aspergillus fumigatus beta-glucosidase (recombinantly produced in Aspergillus oryzae as described in WO 02/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0, 5.0.0, or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-glucosidase activity, beta-xylosidase activity, or beta-glucosidase and beta-xylosidase activity. In one aspect, a subsequence contains at least the polynucleotides encoding the fragments according to the invention or the cDNA thereof.

Variant: The term "variant" means a polypeptide having beta-glucosidase activity, beta-xylosidase activity, or beta-glucosidase and beta-xylosidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67. In the methods of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, Recent progress in the assays of xylanolytic enzymes, *Journal of the Science of Food and Agriculture* 86(11): 1636-1647; Spanikova and Biely, 2006, Glucuronoyl esterase—Novel carbohydrate esterase produced by *Schizophyllum* commune, *FEBS Letters* 580 (19): 4597-4601; Herrmann et al., 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Beta-Glucosidase Activity, Beta-Xylosidase Activity, or Beta-Glucosidase and Beta-Xylosidase Activity In an embodiment, the present invention relates to isolated polypeptides having a sequence identity to the mature polypeptide of SEQ ID NO: 2, SEQ ID NO: 4, SEQ ID NO: 6, SEQ ID NO: 8, SEQ ID NO: 10 or SEQ ID NO: 12 of at least 76%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-glucosidase activity, beta-xylosidase activity, or beta-glucosidase and beta-xylosidase activity. In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, SEQ ID NO: 6, SEQ ID NO: 8, SEQ ID NO: 10 or SEQ ID NO: 12.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10 or SEQ ID NO: 12; or an allelic variant thereof; or is a fragment thereof having beta-glucosidase activity, beta-xylosidase activity, or beta-glucosidase and beta-xylosidase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10 or SEQ ID NO: 12. In another aspect, the polypeptide comprises or consists of amino acids 21 to 774 of SEQ ID NO: 2. In another aspect, the polypeptide comprises or consists of amino acids 20 to 799 of SEQ ID NO: 4. In another aspect, the polypeptide comprises or consists of amino acids 16 to 858 of SEQ ID NO: 6. In another aspect, the polypeptide comprises or consists of amino acids 17 to 740 of SEQ ID NO: 8. In another aspect, the polypeptide comprises or consists of amino acids 17 to 734 of SEQ ID NO: 10. In another aspect, the polypeptide comprises or consists of amino acids 24 to 882 of SEQ ID NO: 12.

In another embodiment, the present invention relates to isolated polypeptides having beta-glucosidase activity, beta-xylosidase activity, or beta-glucosidase and beta-xylosidase activity that are encoded by polynucleotides that hybridize under medium stringency conditions, medium-high stringency conditions, high stringency conditions, or very high stringency conditions with (i) the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, the mature polypeptide coding sequence of SEQ ID NO: 11 or the cDNA sequence thereof, or (ii) the full-length complement of (i) (Sambrook et al., 1989, *Molecular Cloning, A Laboratory Manual,* 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, or SEQ ID NO: 11, or a subsequence thereof, as well as the amino acid sequence of SEQ ID NO: 2, SEQ ID NO: 4, SEQ ID NO: 6, or SEQ ID NO: 8, SEQ ID NO: 10 or SEQ ID NO: 12, or a fragment thereof, may be used to design nucleic acid probes to identify and clone DNA encoding polypeptides having beta-glucosidase activity, beta-xylosidase activity, or beta-glucosidase and beta-xylosidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having beta-glucosidase activity, beta-xylosidase activity, or beta-glucosidase and beta-xylosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, SEQ ID NO: 9 or SEQ ID NO: 11, or a subsequence thereof, the carrier material is used in a Southern blot.

For purposes of the present invention, hybridization indicates that the polynucleotide hybridizes to a labeled nucleic acid probe corresponding to SEQ ID NO: 1 or the cDNA sequence thereof, SEQ ID NO: 3 or the cDNA sequence thereof, SEQ ID NO: 5 or the cDNA sequence thereof, SEQ ID NO: 7 or the cDNA sequence thereof, SEQ ID NO: 9 or the cDNA sequence thereof, SEQ ID NO: 11 or the cDNA sequence thereof; the mature polypeptide coding sequence of SEQ ID NO: 1, SEQ ID NO: 3, SEQ ID NO: 5, SEQ ID NO: 7, SEQ ID NO: 9 or SEQ ID NO: 11; the full-length complement thereof; or a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, the mature polypeptide coding sequence of SEQ ID NO: 11 or the cDNA sequence thereof. In another aspect, the nucleic acid probe is nucleotides 61 to 2490 of SEQ ID NO: 1, nucleotides 58 to 3247 of SEQ ID NO: 3, nucleotides 46 to 3290 of SEQ ID NO: 5, nucleotides 49 to 3221 of SEQ ID NO: 7, nucleotides 49 to 3094 of SEQ ID NO: 9, or nucleotides 70 to 3600 of SEQ ID NO: 11. In another aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, or SEQ ID NO: 12, or the mature polypeptide thereof; or a fragment thereof. In another aspect, the nucleic acid probe is SEQ ID NO: 1 or the cDNA sequence thereof, SEQ ID NO: 3 or the cDNA sequence thereof, SEQ ID NO: 5 or the cDNA sequence thereof, SEQ ID NO: 7 or the cDNA sequence thereof, SEQ ID NO: 9 or the cDNA sequence thereof, or SEQ ID NO: 11 or the cDNA sequence thereof.

In another embodiment, the present invention relates to isolated polypeptides having beta-glucosidase activity, beta-xylosidase activity, or beta-glucosidase and beta-xylosidase activity encoded by polynucleotides having a sequence identity to the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, or the mature polypeptide coding sequence of SEQ ID NO: 11 or the cDNA sequence thereof of at least 76%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, or SEQ ID NO: 12, comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, or SEQ ID NO: 12 is not more than 10, e.g., 1, 2, 3, 4, 5, 6, 7, 8, 9, or 10. The, amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for beta-glucosidase activity, beta-xylosidase activity, or beta-glucosidase and beta-xylosidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Beta-Glucosidase Activity, Beta-Xylosidase Activity, or Beta-Glucosidase and Beta-Xylosidase Activity A polypeptide having beta-glucosidase activity, beta-xylosidase activity, or beta-glucosidase and beta-xylosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

Particularly the polypeptide may be a *Hohenbuehelia* polypeptide.

In another aspect, the polypeptide is a *Hohenbuehelia mastrucata* polypeptide, e.g., a polypeptide obtained from *Hohenbuehelia mastrucata* strain UPSC 3653.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus aculeatus*, or a related organism and thus, for example, may be an allelic or species variant of the polypeptide encoding region of the polynucleotide.

In another embodiment, the present invention relates to isolated polynucleotides comprising or consisting of polynucleotides having a degree of sequence identity to the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, or the mature polypeptide coding sequence of SEQ ID NO: 11 or the cDNA sequence thereof of at least 76%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having beta-glucosidase activity, beta-xylosidase activity, or beta-glucosidase and beta-xylosidase activity.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, or the mature polypeptide coding sequence of SEQ ID NO: 11 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In another embodiment, the present invention relates to isolated polynucleotides encoding polypeptides of the present invention, which hybridize under medium stringency conditions, medium-high stringency conditions, high stringency conditions, or very high stringency conditions with (i) the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, the mature polypeptide coding sequence of SEQ ID NO: 7 or the cDNA sequence thereof, the mature polypeptide coding sequence of SEQ ID NO: 9 or the cDNA sequence thereof, or the mature polypeptide coding sequence of SEQ ID NO: 11 or the cDNA sequence thereof, or (ii) the full-length complement of (i); or allelic variants and subsequences thereof (Sambrook et al., 1989, supra), as defined herein.

In one aspect, the polynucleotide comprises or consists of SEQ ID NO: 1, SEQ ID NO: 3, SEQ ID NO: 5, SEQ ID NO: 7, SEQ ID NO: 9, or SEQ ID NO: 11; or the mature polypeptide coding sequence thereof; or a subsequence thereof that encodes a fragment having beta-glucosidase activity, beta-xylosidase activity, or beta-glucosidase and beta-xylosidase activity.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phospho-ribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*,

*Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In one aspect, the cell is of the genus *Aspergillus*. In another aspect, the cell is *Aspergillus aculeatus*. In another aspect, the cell is *Aspergillus aculeatus* CBS 172.66.

The present invention also relates to methods of producing a polypeptide of the present invention, comprising: (a) cultivating a recombinant host cell of the present invention under conditions conducive for production of the polypeptide; and (b) recovering the polypeptide.

The cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the beta-glucosidase activity, beta-xylosidase activity, or beta-glucosidase and beta-xylosidase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (several) enzymes selected from the group consisting of a cellulase, a hemicellulase, an expansin, an esterase, a laccase, a ligninolytic enzyme, a pectinase, a peroxidase, a protease, and a swollenin.

The compositions may be prepared in accordance with methods known in the art and may be in the form of a liquid or a dry composition. The polypeptide to be included in the composition may be stabilized in accordance with methods known in the art.

The compositions may be a fermentation broth formulation or a cell composition, as described herein. Consequently, the present invention also relates to fermentation broth formulations and cell compositions comprising a polypeptide having beta-glucosidase activity, beta-xylosidase activity, or beta-glucosidase and beta-xylosidase activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or non-viable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as cellobiohydrolase, endoglucanase, beta-glucosidase, endo-beta-1,3(4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextrinnases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following processes for using the polypeptides having beta-glucosidase activity, beta-xylosidase activity, or beta-glucosidase and beta-xylosidase activity, or compositions thereof.

The present invention also relates to processes for degrading a cellulosic material or xylan-containing material, comprising: treating the cellulosic material or xylan-containing material with an enzyme composition in the presence of a polypeptide having beta-glucosidase activity, beta-xylosidase activity, or beta-glucosidase and beta-xylosidase activity of the present invention. In one aspect, the processes further comprise recovering the degraded or converted cellulosic material or xylan-containing material. Soluble products of degradation or conversion of the cellulosic material or xylan-containing material can be separated from insoluble cellulosic material or xylan-containing material using a method known in the art such as, for example, centrifugation, filtration, or gravity settling.

The present invention also relates to processes of producing a fermentation product, comprising: (a) saccharifying a cellulosic material or xylan-containing material with an enzyme composition in the presence of a polypeptide having beta-glucosidase activity, beta-xylosidase activity, or beta-glucosidase and beta-xylosidase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of the present invention. In one aspect, the fermenting of the cellulosic material or xylan-containing material produces a fermentation product. In another aspect, the processes further comprise recovering the fermentation product from the fermentation.

The processes of the present invention can be used to saccharify the cellulosic material or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material or xylan-containing material typically involves pretreatment, enzymatic hydrolysis (saccharification), and fermentation.

The processing of the cellulosic material or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material or xylan-containing material to fermentable sugars, e.g., glucose, cellobiose, and pentose monomers, and then ferment the fermentable sugars to ethanol. In SSF, the enzymatic hydrolysis of the cellulosic material or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material or xylan-containing material to fermentable sugars and to convert the fermentable sugars into a final product (Lynd et al., 2002, Microbial cellulose utilization: Fundamentals and biotechnology, Microbiol. Mol. Biol. Reviews 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, Optimal control in fed-batch reactor for the cellobiose hydrolysis, *Acta Scientiarum. Technology* 25: 33-38; Gusakov and Sinitsyn, 1985, Kinetics of the enzymatic hydrolysis of cellulose: 1. A mathematical model for a batch reactor process, *Enz. Microb. Technol.* 7: 346-352), an attrition reactor (Ryu and Lee, 1983, Bioconversion of waste cellulose by using an attrition bioreactor, *Biotechnol. Bioeng.* 25: 53-65), or a reactor with intensive stirring induced by an electromagnetic field (Gusakov et al., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material or xylan-containing material can also be subjected to particle size reduction, sieving, presoaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material or xylan-containing material is heated to disrupt the plant cell wall components, including lignin, hemicellulose, and cellulose to make the cellulose and other fractions, e.g., hemicellulose, accessible to enzymes. The cellulosic material or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Application Publication No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Application Publication No. 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material or xylan-containing material is present during pretreatment in amounts preferably between 10-80 wt. %, e.g., 20-70 wt. % or 30-60 wt. %, such as around 40 wt. %. The pretreated cellulosic material or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having beta-glucosidase activity, beta-xylosidase activity, or beta-glucosidase and beta-xylosidase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt. %, e.g., about 10 to about 40 wt. % or about 20 to about 30 wt. %.

The enzyme compositions can comprise any protein useful in degrading the cellulosic material or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having beta-glucosidase activity, beta-xylosidase activity, or beta-glucosidase and beta-xylosidase activity depend on several factors including, but not limited to, the mixture of component cellulolytic and/or hemicellulolytic enzymes, the cellulosic material or xylan-containing material, the concentration of cellulosic material or xylan-containing material, the pretreatment(s) of the cellulosic material or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material or xylan-containing material.

In another aspect, an effective amount of a polypeptide having beta-glucosidase activity, beta-xylosidase activity, or beta-glucosidase and beta-xylosidase activity to the cellulosic material or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material or xylan-containing material.

In another aspect, an effective amount of a polypeptide having beta-glucosidase activity, beta-xylosidase activity, or beta-glucosidase and beta-xylosidase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 2005/093050); *Thermobifida fusca* endoglucanase III (WO 2005/093050); and *Thermobifida fusca* endoglucanase V (WO 2005/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no.

Z33381), *Aspergillus* aculeatus endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the methods of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{4}$ to about $10^{-1}$, about $10^{-3}$ to about $10^{-1}$, or about $10^{-3}$ to about $10^{-2}$. In another aspect, an effective amount of such a compound described above is about 0.1 microM to about 1 M, e.g., about 0.5 microM to about 0.75 M, about 0.75 microM to about 0.5 M, about 1 microM to about 0.25 M, about 1 microM to about 0.1 M, about 5 microM to about 50 mM, about 10 microM to about 25 mM, about 50 microM to about 25 mM, about 10 microM to about 10 mM, about 5 microM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8×212).

Examples of acetylxylan esterases useful in the processes of the present invention include, but are not limited to, acetylxylan esterases from *Aspergillus aculeatus* (WO 2010/108918), *Chaetomium globosum* (UniProt accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria*

*nodorum* (UniProt accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (UniProt accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8×211), and *Trichoderma reesei* (UniProt accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*.

In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium* phytofermentans. In another more preferred aspect, the bacterium is *Clostridium thermocellum*. In another more preferred aspect, the bacterium is *Geobacilus* sp. In another more preferred aspect, the bacterium is a Thermoanaerobacter. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas* mobilis strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka et al., 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy* 13(1-2): 83-114.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 20 of SEQ ID NO: 2, amino acids 1 to 19 of SEQ ID NO: 4, amino acids 1 to 15 of SEQ ID NO: 6, amino acids 1 to 16 of SEQ ID NO: 8, amino acids 1 to 16 of SEQ ID NO: 10, amino acids 1 to 23 of SEQ ID NO: 12. The polynucleotides may further comprise a gene encoding a protein, which is operably linked to the signal peptide. The protein is preferably foreign to the signal peptide.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

EXAMPLES

Strains

*Hohenbuehelia mastrucata* strain UPSC 3653 (collected in Sweden Nov. 28, 1995), was used as the source of Family GH3 genes.

Media

YP+2% glucose medium was composed of 1% yeast extract, 2% peptone and 2% glucose.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 microliters/500 ml) was added.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Example 1

Genomic DNA Extraction

To generate genomic DNA for PCR amplification, the different fungal strains (see strains above) were propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, Calif., USA). Briefly a FastDNA® SPIN Kit for Soil (Qbiogene, Inc., Carlsbad, Calif., USA) was used in a FastPrep® 24 Homogenization System (MP Biosciences, Santa Ana, Calif., USA). Two ml of fungal material from the above cultures were harvested by centrifugation at 14,000×g for 2 minutes. The supernatant was removed and the pellet resuspended in 500 microliters of deionized water. The suspension was transferred to a Lysing Matrix E FastPrep® tube (Qbiogene, Inc., Carlsbad, Calif., USA) and 790 microliters of sodium phosphate buffer and 100 microliters of MT buffer from the FastDNA® SPIN Kit were added to the tube. The sample was then secured in the FastPrep® Instrument (Qbiogene, Inc., Carlsbad, Calif., USA) and processed for 60 seconds at a speed of 5.5 m/sec. The sample was then centrifuged at 14000×g for two minutes and the supernatant transferred to a clean EPPENDORF® tube. A 250 microliter volume of PPS reagent from the FastDNA® SPIN Kit was added and then the sample was mixed gently by inversion. The sample was again centrifuged at 14000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 microliter volume of the supernatant was removed and discarded and then the remaining sample was resuspended in the matrix. The sample was then transferred to a SPIN filter tube from the FastDNA® SPIN Kit and centrifuged at 14000×g for 1 minute. The catch tube was emptied and the remaining matrix suspension added to the SPIN filter tube. The sample was again centrifuged (14000×g, 1 minute). A 500 microliter volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14000×g for 2 minutes to "dry" the matrix of residual SEWS-M wash solution. The SPIN filter was placed in a fresh catch tube and allowed to air dry for 5 minutes at room temperature. The matrix was gently resuspended in 100 microliters of DES (DNase/Pyrogen free water) with a pipette tip. The unit was centrifuged (14000×g, 1 minute) to elute the genomic DNA followed by elution with 100 microliters of 10 mM Tris, 0.1 mM EDTA, pH 8.0 by renewed centrifugation at 14000×g for 1 minute and the eluates were combined. The concentration of the DNA harvested from the catch tube was measured by a UV spectrophotometer at 260 nm.

Example 2

Genome Sequencing, Assembly and Annotation

The extracted genomic DNA samples were delivered to Fasteris (Fasteris SA, Geneva, Switzerland) or Beijing Genome Institute (BGI, Shenzhen, China) for genome sequencing using ILLUMINA® GA2 System (Illumina, Inc., San Diego, Calif., USA). The raw reads coming from Fasteris were assembled in house using the Abyss assembler (bcg-sc.ca/platform/bioinfo/software/abyss) and the others were assembled at BGI using in house program SOAPdenovo. The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.21 (National Center for Biotechnology Information (NCBI), Bethesda, Md., USA) and HMMER version 2.3.2 (sanger.ac.uk/resources/software/) were used to predict function based on structural homology. The family GH3 enzyme candidates were identified directly by analysis of the Blast results. Agene (Munch and Krogh, 2006, *BMC Bioinformatics* 7: 263) and SignalP (Nielsen et al., 1997, *Protein Engineering* 10:1-6) were used to identify start codons.

Example 3

Construction of an *Aspergillus oryzae* Expression Vector Containing Genomic Sequences Encoding a Family GH3 Polypeptide Having Beta-Glucosidase Activity, Beta-Xylosidase Activity, or Beta-Glucosidase and Beta-Xylosidase Activity Synthetic oligonucleotide primers shown below (SEQ ID NO: 13 to SEQ ID NO: 24) are designed to PCR amplify GH3 genes from the genomic DNA prepared in Example 1. An IN-FUSION™ Cloning Kit (Clontech, Mountain View, Calif., USA) is used to clone the fragments directly into the expression vector pDau109 (WO 2005/042735).

```
Primer GH3_126f
                                            (SEQ ID NO: 13)
ACACAACTGGGGATCCACCATGTCTCGGTTATTCGCCAGAGTCGCTCT
```

```
Primer GH3_126r
                                            (SEQ ID NO: 14)
AGATCTCGAGAAGCTTATTTCGGCGATGGGGTCGAAGTTGAGT Primer GH3_249f
                                            (SEQ ID NO: 15)
ACACAACTGGGGATCCACCATGAGAGGGCTACTGTCTTTTACGCTCCTTT
CA Primer GH3_249r
                                            (SEQ ID NO: 16)
AGATCTCGAGAAGCTTATGTAACCGTCAGCGTCGCATTCGCA Primer GH3_250f
                                            (SEQ ID NO: 17)
ACACAACTGGGGATCCACCATGGCCACCCTCACCCTGCTCA Primer GH3_250r
                                            (SEQ ID NO: 18)
AGATCTCGAGAAGCTTAAACAGGAATGCTGCCCTTCAGCCTGAAATCC Primer GH3_251f
                                            (SEQ ID NO: 19)
ACACAACTGGGGATCCACCATGGCTCGCTTGATCTGCTTCCTCTCTTTGC Primer GH3_251r
                                            (SEQ ID NO: 20)
AGATCTCGAGAAGCTTAGAAGGTTGCCGTAAGGCGTATATCCTTGATCGA Primer GH3_252f
                                            (SEQ ID NO: 21)
ACACAACTGGGGATCCACCATGGCACGATTGATCTATCTTTCCTGGCTGG
T Primer GH3_252r
                                            (SEQ ID NO: 22)
AGATCTCGAGAAGCTTAAAGACGAAAAGTCGTATTGAGCCGAATGTCCTT
GC Primer GH3_253f
                                            (SEQ ID NO: 23)
ACACAACTGGGGATCCACCATGGCCAAGCTTACACCCTTGCTCCT Primer GH3_253r
                                            (SEQ ID NO: 24)
AGATCTCGAGAAGCTTATAACGGAAGCTCCCCATGTAGTCGAAGGT
```

PCR reactions are carried out with genomic DNA prepared from Example 1 for amplification of the genes identified in Example 2. The PCR reaction are composed of 1 microliter of genomic DNA, 1 microliter of primer forward (f) (50 microM); 1 microliter of primer reverse (r) (50 microM); 10 microliters of 5×HF buffer (Finnzymes Oy, Finland), 2 microliters of 10 mM dNTP; 1 microliter of PHUSION® DNA polymerase (Finnzymes Oy, Finland), and PCR-grade water up to 50 microliters. Primer GH3-126f and GH3-126r are used simultaneously to PCR amplified SEQ ID NO:1; Primer GH3-249f and GH3-249r are used simultaneously to PCR amplified SEQ ID NO:3; Primer GH3-250f and GH3-250r are used simultaneously to PCR amplified SEQ ID NO:5; Primer GH3-251f and GH3-251r are used simultaneously to PCR amplified SEQ ID NO:7; Primer GH3-252f and GH3-252r are used simultaneously to PCR amplified SEQ ID NO:9; and Primer GH3-253f: The PCR reactions are performed using a DYAD PCR machine (Bio-Rad Laboratories, Inc., Hercules, Calif., USA) programmed for 2 minutes at 98° C. followed by 20 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products are isolated by 1.0% agarose gel electrophoresis using 40 mM Tris base, 20 mM sodium acetate, 1 mM disodium EDTA (TAE) buffer where approximately 2.2 to 3.6 kb PCR product bands are excised from the gels and purified using a GFX® PCR DNA and Gel Band Purification Kit (GE Healthcare, United Kingdom) according to manufacturer's instructions. DNA corresponding to the GH3 genes are cloned into the expression vector pDAu109 (WO 2005/042735) linearized with Bam HI and Hind III, using an IN-FUSION™ Dry-Down PCR Cloning Kit (BD Biosciences, Palo Alto, Calif., USA) according to the manufacturer's instructions.

A 2.5 microliter volume of the five times diluted ligation mixture is used to transform *E. coli* TOP10 chemically competent cells (Invitrogen, Carlsbad, Calif., USA). Five colonies are selected on LB agar plates containing 100 micrograms of ampicillin per ml and cultivated overnight in 3 ml of LB medium supplemented with 100 micrograms of ampicillin per ml. Plasmid DNA is purified using an E.Z.N.A.® Plasmid Mini Kit (Omega Bio-Tek, Inc., Norcross, Ga., USA) according to the manufacturer's instructions. The GH3 gene sequences are verified by Sanger sequencing with an Applied Biosystems Model 3700 Automated DNA Sequencer using version 3.1 BIG-DYE™ terminator chemistry (Applied Biosystems, Inc., Foster City, Calif., USA). Nucleotide sequence data are scrutinized for quality and all sequences are compared to each other with assistance of PHRED/PHRAP software (University of Washington, Seattle, Wash., USA).

Example 4

Characterization of the Genomic Sequences Encoding GH3 Polypeptides Having Beta-Glucosidase Activity, Beta-Xylosidase Activity, or Beta-Glucosidase and Beta-Xylosidase Activity The nucleotide sequence and deduced amino acid sequence of the *Hohenbuehelia mastrucata* GH3 gene are shown in SEQ ID NO: 1 and SEQ ID NO: 2, respectively. The coding sequence is 2490 bp including the stop codon and is interrupted by three introns of 53 bp (nucleotides 265 to 317), 60 bp (nucleotides 1130 to 1189), and 52 bp (nucleotides 1737 to 1788). The encoded predicted protein is 774 amino acids. Using the SignalP program v.3 (Nielsen et al., 1997, supra), a signal peptide of 20 residues was predicted. The predicted mature protein contains 754 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Hohenbuehelia mastrucata* gene encoding the GH3 polypeptide having beta-glucosidase activity, beta-xylosidase activity, or beta-glucosidase and beta-xylosidase activity shares 63.29% identity (excluding gaps) to the deduced amino acid sequence of a GH3 family protein from *Moniliophtora perniciosa* (SwissProt accession number E2LXM8).

The nucleotide sequence and deduced amino acid sequence of the *Hohenbuehelia mastrucata* GH3 gene are shown in SEQ ID NO: 3 and SEQ ID NO: 4, respectively. The coding sequence is 3247 bp including the stop codon and is interrupted by fifteen introns of 49 bp (nucleotides 225 to 273), 52 bp (nucleotides 353 to 404), 63 bp (nucleotides 550 to 612), 53 bp (nucleotides 962 to 1014), 64 bp (nucleotides 1155 to 1218), 63 bp (nucleotides 1236 to 1298), 49 bp (nucleotide 1474 to 1522), 45 bp (nucleotides 1616 to 1660), 59 bp (nucleotides 1837 to 1895), 71 bp (nucleotides 2284 to 2354), 55 bp (nucleotides 2433 to 2487), 63 bp (nucleotides 2616 to 2678), 52 bp (nucleotides 2747 to 2798), 58 bp (nucleotides 2905 to 2962), and 51 bp (nucleotides 3040 to 3090). The encoded predicted protein is 799 amino acids. Using the SignalP program v.3 (Nielsen et al., 1997, supra), a signal peptide of 19 residues was predicted. The predicted mature protein contains 780 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Hohenbuehelia mastrucata* gene encoding the GH3 polypeptide having beta-glucosidase activity, beta-xylosidase activity, or beta-glucosidase and beta-xylosidase activity shares 69.97% identity (excluding gaps) to the deduced amino acid sequence of a GH3 family protein from *Postia placenta* (SwissProt accession number B8P3Z6).

The nucleotide sequence and deduced amino acid sequence of the *Hohenbuehelia mastrucata* GH3 gene are shown in SEQ ID NO: 5 and SEQ ID NO: 6, respectively. The coding sequence is 3290 bp including the stop codon and is interrupted by thirteen introns of 48 bp (nucleotides 409 to 456), 54 bp (nucleotides 645 to 698), 57 bp (nucleotides 836 to 892), 50 bp (nucleotides 920 to 969), 53 bp (nucleotides 1040 to 1092), 54 bp (nucleotides 1218 to 1271), 56 bp (nucleotides 1353 to 1408), 50 bp (nucleotides 1468 to 1517), 50 bp (nucleotides 1629 to 1678), 53 bp (nucleotides 2030 to 2082), 60 bp (nucleotides 2262 to 2321), 61 bp (nucleotides 2677 to 2737), and 67 bp (nucleotides 2981 to 3047). The encoded predicted protein is 858 amino acids. Using the SignalP program v.3 (Nielsen et al., 1997, supra), a signal peptide of 15 residues was predicted. The predicted mature protein contains 843 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Hohenbuehelia mastrucata* gene encoding the GH3 polypeptide having beta-glucosidase activity, beta-xylosidase activity, or beta-glucosidase and beta-xylosidase activity shares 75.92% identity (excluding gaps) to the deduced amino acid sequence of a GH3 family protein from *Laccaria bicolor* (SwissProt accession number B0D734).

The nucleotide sequence and deduced amino acid sequence of the *Hohenbuehelia mastrucata* GH3 gene are shown in SEQ ID NO: 7 and SEQ ID NO: 8, respectively. The coding sequence is 3221 bp including the stop codon and is interrupted by fifteen introns of 49 bp (nucleotides 59 to 107), 58 bp (nucleotides 207 to 264), 56 bp (nucleotides 467 to 522), 55 bp (nucleotides 551 to 605), 216 bp (nucleotides 641 to 856), 56 bp (nucleotides 1053 to 1108), 54 bp (nucleotides 1221 to 1274), 63 bp (nucleotides 1445 to 1507), 63 bp (nucleotides 1568 to 1630), 53 bp (nucleotides 1927 to 1979), 60 bp (nucleotides 2145 to 2204), 40 bp (nucleotides 2308 to 2347), 52 bp (nucleotides 2552 to 2603), 66 bp (nucleotides 2658 to 2723), and 57 bp (nucleotides 3062 to 3118). The encoded predicted protein is 740 amino acids. Using the SignalP program v.3 (Nielsen et al., 1997, supra), a signal peptide of 16 residues was predicted. The predicted mature protein contains 724 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLO- SUM62 matrix. The alignment showed that the deduced amino acid sequence of the *Hohenbuehelia mastrucata* gene encoding the GH3 polypeptide having beta-glucosidase activity, beta-xylosidase activity, or beta-glucosidase and beta-xylosidase activity shares 72.66% identity (excluding gaps) to the deduced amino acid sequence of a GH3 family protein from *Laccaria bicolor* (SwissProt accession number B0D3B6).

The nucleotide sequence and deduced amino acid sequence of the *Hohenbuehelia mastrucata* GH3 gene are shown in SEQ ID NO: 9 and SEQ ID NO: 10, respectively. The coding sequence is 3094 bp including the stop codon and is interrupted by fifteen introns of 55 bp (nucleotides 59 to 113), 55 bp (nucleotides 213 to 267), 51 bp (nucleotides 470 to 520), 58 bp (nucleotides 549 to 606), 124 bp (nucleotides 642 to 765), 53 bp (nucleotides 962 to 1014), 63 bp (nucleotides 1127 to 1189), 48 bp (nucleotides 1360 to 1407), 50 bp (nucleotides 1468 to 1517), 57 bp (nucleotides 1814 to 1870), 60 bp (nucleotides 2036 to 2095), 57 bp (nucleotides 2184 to 2240), 51 bp (nucleotides 2445 to 2495), 55 bp (nucleotides 2550 to 2604), and 52 bp (nucleotides 2934 to 2985). The encoded predicted protein is 734 amino acids. Using the SignalP program v.3 (Nielsen et al., 1997, supra), a signal peptide of 16 residues was predicted. The predicted mature protein contains 718 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Hohenbuehelia mastrucata* gene encoding the GH3 polypeptide having beta-glucosidase activity, beta-xylosidase activity, or beta-glucosidase and beta-xylosidase activity shares 61.71% identity (excluding gaps) to the deduced amino acid sequence of a GH3 family protein from *Laccaria bicolor* (SwissProt accession number B0D3B6).

The nucleotide sequence and deduced amino acid sequence of the *Hohenbuehelia mastrucata* GH3 gene are shown in SEQ ID NO: 11 and SEQ ID NO: 12, respectively. The coding sequence is 3600 bp including the stop codon and is interrupted by seventeen introns of 54 bp (nucleotides 469 to 522), 54 bp (nucleotides 658 to 711), 65 bp (nucleotides 783 to 847), 69 bp (nucleotides 1012 to 1080), 52 bp (nucleotides 1151 to 1202), 53 bp (nucleotides 1328 to 1380), 56 bp (nucleotides 1462 to 1517), 66 bp (nucleotides 1577 to 1642), 64 bp (nucleotides 1754 to 1817), 55 bp (nucleotides 2135 to 2189), 54 bp (nucleotides 2218 to 2271), 52 bp (nucleotides 2427 to 2478), 60 bp (nucleotides 2618 to 2677), 31 bp (nucleotides 2887 to 2917), 49 bp (nucleotides 2949 to 2997), 55 bp (nucleotides 3174 to 3228), and 62 bp (nucleotides 3296 to 3357). The encoded predicted protein is 882 amino acids. Using the SignalP program v.3 (Nielsen et al., 1997, supra), a signal peptide of 23 residues was predicted. The predicted mature protein contains 859 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Hohenbuehelia mastrucata* gene encoding the GH3 polypeptide having beta-glucosidase activity, beta-xylosidase activity, or beta-glucosidase and beta-xylosidase activity shares 68.90% identity (excluding gaps) to the deduced amino acid sequence of a GH3 family protein from *Laccaria bicolor* (SwissProt accession number B0D734).

The invention claimed is:

1. An isolated polypeptide having beta-glucosidase and beta-xylosidase activity selected from the group consisting of:
   (a) a polypeptide having at least 95% sequence identity to the sequence of amino acids 21-774 of SEQ ID NO: 2;
   (b) a variant of the sequence of amino acids 21-774 of SEQ ID NO: 2 comprising a substitution, deletion, and/or insertion at one or more positions and having at least 95% sequence identity to amino acids 21-774 of SEQ ID NO: 2; and
   (c) a fragment of the polypeptide of (a) or (b) that has beta-glucosidase and beta-xylosidase activity.

2. The polypeptide of claim 1 having at least 95% sequence identity to the sequence of amino acids 21-774 of SEQ ID NO: 2.

3. The polypeptide of claim 1 having at least 97% sequence identity to the sequence of amino acids 21-774 of SEQ ID NO: 2.

4. The polypeptide of claim 1 having at least 99% sequence identity to the sequence of amino acids 21-774 of SEQ ID NO: 2.

5. The polypeptide of claim 1, wherein the polypeptide consists of the sequence of amino acids 21-774 of SEQ ID NO: 2.

6. A composition comprising a polypeptide of claim 1 and an enzyme selected from the group consisting of a cellulase, a hemicellulase, an expansin, an esterase, a laccase, a ligninolytic enzyme, a pectinase, a peroxidase, a protease, and a swollenin.

7. A composition comprising a polypeptide of claim 2 and an enzyme selected from the group consisting of a cellulase, a hemicellulase, an expansin, an esterase, a laccase, a ligninolytic enzyme, a pectinase, a peroxidase, a protease, and a swollenin.

8. A composition comprising a polypeptide of claim 3 and an enzyme selected from the group consisting of a cellulase, a hemicellulase, an expansin, an esterase, a laccase, a ligninolytic enzyme, a pectinase, a peroxidase, a protease, and a swollenin.

9. A composition comprising a polypeptide of claim 4 and an enzyme selected from the group consisting of a cellulase, a hemicellulase, an expansin, an esterase, a laccase, a ligninolytic enzyme, a pectinase, a peroxidase, a protease, and a swollenin.

10. A composition comprising a polypeptide of claim 5 and an enzyme selected from the group consisting of a cellulase, a hemicellulase, an expansin, an esterase, a laccase, a ligninolytic enzyme, a pectinase, a peroxidase, a protease, and a swollenin.

11. A process for degrading or converting a cellulosic material or xylan-containing material, wherein the process comprises treating the cellulosic material or xylan-containing material with an enzyme composition in the presence of the polypeptide of claim 1.

12. A process for producing a fermentation product, wherein the process comprises:
   (a) saccharifying a cellulosic material or xylan-containing material with an enzyme composition in the presence of the polypeptide of claim 1; and
   (b) fermenting the saccharified cellulosic material or xylan-containing material with one or more fermenting microorganisms to produce the fermentation product.

13. The process of claim 12, further comprising recovering the fermentation product from the fermentation.

14. A process for producing a fermentation product, wherein the process comprises:
   (a) saccharifying a cellulosic material or xylan-containing material with an enzyme composition in the presence of the polypeptide of claim 3; and
   (b) fermenting the saccharified cellulosic material or xylan-containing material with one or more fermenting microorganisms to produce the fermentation product.

15. The process of claim 14, further comprising recovering the fermentation product from the fermentation.

16. A process for producing a fermentation product, wherein the process comprises:
   (a) saccharifying a cellulosic material or xylan-containing material with an enzyme composition in the presence of the polypeptide of claim 5; and
   (b) fermenting the saccharified cellulosic material or xylan-containing material with one or more fermenting microorganisms to produce the fermentation product.

17. The process of claim 16, further comprising recovering the fermentation product from the fermentation.

18. A recombinant host cell comprising an isolated polynucleotide encoding the polypeptide of claim 1, wherein the isolated polynucleotide is operably linked to one or more control sequences that direct the production of the polypeptide.

19. A method of producing a polypeptide having beta-glucosidase and beta-xylosidase activity, wherein the method comprises:
   (a) cultivating the host cell of claim 18 under conditions conducive for production of the polypeptide; and
   (b) recovering the polypeptide.

20. A whole broth formulation or cell culture composition comprising the polypeptide of claim 1.

* * * * *